(12) United States Patent
Stroup et al.

(10) Patent No.: US 9,211,134 B2
(45) Date of Patent: Dec. 15, 2015

(54) WRIST ASSEMBLY FOR ARTICULATING LAPAROSCOPIC SURGICAL INSTRUMENTS

(75) Inventors: David Karl Stroup, El Cajon, CA (US); Arthur Deptala, Spring Valley, CA (US)

(73) Assignee: CareFusion 2200, Inc., San Diego, CA (US)

( * ) Notice: Subject to any disclaimer, the term of this patent is extended or adjusted under 35 U.S.C. 154(b) by 862 days.

(21) Appl. No.: 13/442,524

(22) Filed: Apr. 9, 2012

(65) Prior Publication Data

US 2013/0267936 A1 Oct. 10, 2013

(51) Int. Cl.
*A61B 17/00* (2006.01)
*A61B 17/29* (2006.01)

(52) U.S. Cl.
CPC ....... *A61B 17/29* (2013.01); *A61B 2017/00314* (2013.01); *A61B 2017/2903* (2013.01); *A61B 2017/2929* (2013.01)

(58) Field of Classification Search
CPC ............... A61B 1/0055; A61B 2017/320032; A61B 2017/003; A61B 19/26; A61B 17/29; A61B 2017/00314; A61B 2017/2903; A61B 2017/2929
See application file for complete search history.

(56) References Cited

U.S. PATENT DOCUMENTS

| | | | |
|---|---|---|---|
| 3,190,286 A | 6/1965 | Stokes | |
| 3,266,059 A | 8/1966 | Stelle | |
| 3,557,780 A | 1/1971 | Sato | |
| 3,739,770 A | 6/1973 | Mori | |
| 3,788,303 A | 1/1974 | Hall | |
| 3,799,151 A | 3/1974 | Fukaumi et al. | |
| 4,271,845 A | 6/1981 | Chikashige et al. | |
| 4,294,233 A | 10/1981 | Takahashi | |
| 4,347,837 A | 9/1982 | Hosono | |
| 4,351,323 A | 9/1982 | Ouchi et al. | |
| 4,353,358 A | 10/1982 | Emerson | |
| 4,432,349 A | 2/1984 | Oshiro | |
| 4,461,282 A | 7/1984 | Ouchi et al. | |
| 4,530,568 A | 7/1985 | Haduch et al. | |
| 4,557,254 A | 12/1985 | Yamaguchi | |
| 4,559,928 A | 12/1985 | Takayama | |
| 4,577,621 A | 3/1986 | Patel | |

(Continued)

FOREIGN PATENT DOCUMENTS

EP 0 634 144 A1 7/1994
EP 0 836 833 A2 4/1998

(Continued)

OTHER PUBLICATIONS

PCT International Search Report and Written Opinion for International No. PCT/US2013/029534, mailing date May 17, 2013.

*Primary Examiner* — Gary Jackson
*Assistant Examiner* — Scott T Luan
(74) *Attorney, Agent, or Firm* — Brinks Gilson & Lione

(57) ABSTRACT

An articulating laparoscopic instrument including a handle, an outer shaft, an end effector, and a wrist assembly. The wrist assembly connects the end effector to the shaft and includes torque and articulation mechanisms. The torque mechanism includes a plurality of links disposed over the rod and connected with one another in a pivotable yet rotationally locked fashion. The articulation mechanism includes a plurality of articulation member disposed over the rod to collectively define a deflection section. The links freely rotate relative to the articulation members, with the rod and links collectively bending in response to a change in shape of the deflection section.

20 Claims, 25 Drawing Sheets

(56) References Cited

U.S. PATENT DOCUMENTS

| | | |
|---|---|---|
| 4,651,718 A | 3/1987 | Collins et al. |
| 4,653,476 A | 3/1987 | Bonnet |
| 4,654,028 A | 3/1987 | Suma |
| 4,686,963 A | 8/1987 | Cohen et al. |
| 4,688,555 A | 8/1987 | Wardle |
| 4,700,693 A | 10/1987 | Lia et al. |
| 4,708,434 A | 11/1987 | Tsuno |
| 4,726,355 A | 2/1988 | Okada |
| 4,728,020 A | 3/1988 | Green et al. |
| 4,762,118 A | 8/1988 | Lia et al. |
| 4,762,119 A | 8/1988 | Allred, III et al. |
| 4,763,669 A | 8/1988 | Jaeger |
| 4,773,395 A | 9/1988 | Suzuki et al. |
| 4,774,949 A | 10/1988 | Fogarty |
| 4,790,294 A | 12/1988 | Allred, III et al. |
| 4,796,607 A | 1/1989 | Allred, III et al. |
| 4,846,573 A | 7/1989 | Taylor et al. |
| 4,856,518 A | 8/1989 | McFadden |
| 4,869,414 A | 9/1989 | Green et al. |
| 4,873,965 A | 10/1989 | Danieli |
| 4,880,015 A | 11/1989 | Nierman |
| 4,882,777 A | 11/1989 | Narula |
| 4,890,602 A | 1/1990 | Hake |
| 4,909,789 A | 3/1990 | Taguchi et al. |
| 4,911,148 A | 3/1990 | Sosnowski et al. |
| 4,926,860 A | 5/1990 | Stice et al. |
| 4,941,454 A | 7/1990 | Wood et al. |
| 4,947,827 A | 8/1990 | Opie et al. |
| 4,962,877 A | 10/1990 | Hervas |
| 4,977,887 A | 12/1990 | Gouda |
| 4,986,257 A | 1/1991 | Chikama |
| 4,996,974 A | 3/1991 | Ciarlei |
| 5,002,041 A | 3/1991 | Chikama |
| 5,005,558 A | 4/1991 | Aomori |
| 5,007,406 A | 4/1991 | Takahashi et al. |
| 5,058,568 A | 10/1991 | Irion et al. |
| 5,106,381 A | 4/1992 | Chikama |
| 5,143,475 A | 9/1992 | Chikama |
| 5,174,277 A | 12/1992 | Matsumaru |
| 5,176,126 A | 1/1993 | Chikama |
| 5,178,129 A | 1/1993 | Chikama et al. |
| 5,179,934 A | 1/1993 | Nagayoshi et al. |
| 5,203,772 A | 4/1993 | Hammerslag et al. |
| 5,209,747 A | 5/1993 | Knoepfler |
| 5,220,911 A | 6/1993 | Tamura |
| 5,237,985 A | 8/1993 | Hodgson et al. |
| 5,251,611 A | 10/1993 | Zehel et al. |
| 5,254,130 A | 10/1993 | Poncet et al. |
| 5,255,668 A | 10/1993 | Umeda |
| 5,271,381 A | 12/1993 | Ailinger et al. |
| 5,271,382 A | 12/1993 | Chikama |
| 5,275,608 A | 1/1994 | Forman et al. |
| 5,284,128 A | 2/1994 | Hart |
| 5,299,559 A | 4/1994 | Bruce et al. |
| 5,308,324 A | 5/1994 | Hammerslag et al. |
| 5,312,023 A | 5/1994 | Green et al. |
| 5,318,526 A | 6/1994 | Cohen |
| 5,330,502 A | 7/1994 | Hassler et al. |
| 5,346,504 A | 9/1994 | Ortiz et al. |
| 5,354,311 A | 10/1994 | Kambin et al. |
| 5,383,888 A | 1/1995 | Zvenyatsky et al. |
| 5,386,818 A | 2/1995 | Schneebaum et al. |
| 5,395,033 A | 3/1995 | Byrne et al. |
| 5,395,367 A | 3/1995 | Wilk |
| 5,403,342 A | 4/1995 | Tovey et al. |
| 5,405,344 A | 4/1995 | Williamson et al. |
| 5,409,498 A | 4/1995 | Braddock et al. |
| 5,411,519 A | 5/1995 | Tovey et al. |
| 5,417,203 A | 5/1995 | Tovey et al. |
| 5,439,478 A | 8/1995 | Palmer |
| 5,441,494 A | 8/1995 | Ortiz |
| 5,448,989 A | 9/1995 | Heckele |
| 5,452,836 A | 9/1995 | Huitema et al. |
| 5,454,827 A | 10/1995 | Aust et al. |
| 5,456,401 A | 10/1995 | Green et al. |
| 5,458,606 A | 10/1995 | Cohen et al. |
| 5,467,763 A | 11/1995 | McMahon et al. |
| 5,468,250 A | 11/1995 | Paraschac et al. |
| 5,469,840 A | 11/1995 | Tanii et al. |
| 5,472,017 A | 12/1995 | Kovalcheck |
| 5,490,819 A | 2/1996 | Nicholas et al. |
| 5,501,654 A | 3/1996 | Failla et al. |
| 5,514,157 A | 5/1996 | Nicholas et al. |
| 5,520,678 A | 5/1996 | Heckele et al. |
| 5,531,686 A | 7/1996 | Lundquist et al. |
| 5,540,706 A | 7/1996 | Aust et al. |
| 5,549,542 A | 8/1996 | Kovalcheck |
| 5,549,637 A | 8/1996 | Crainich |
| 5,562,682 A | 10/1996 | Oberlin et al. |
| 5,582,617 A | 12/1996 | Klieman et al. |
| 5,599,151 A | 2/1997 | Daum et al. |
| 5,607,435 A | 3/1997 | Sachdeva et al. |
| 5,609,601 A | 3/1997 | Kolesa et al. |
| 5,618,294 A | 4/1997 | Aust et al. |
| 5,620,415 A | 4/1997 | Lucey et al. |
| 5,620,447 A | 4/1997 | Smith et al. |
| 5,624,380 A | 4/1997 | Takayama et al. |
| 5,632,433 A | 5/1997 | Grant et al. |
| 5,643,294 A | 7/1997 | Tovey et al. |
| 5,649,955 A | 7/1997 | Hashimoto et al. |
| 5,649,957 A | 7/1997 | Levin |
| 5,656,029 A | 8/1997 | Imran et al. |
| 5,669,926 A | 9/1997 | Aust et al. |
| 5,674,197 A | 10/1997 | van Muiden et al. |
| 5,681,263 A | 10/1997 | Flesch |
| 5,700,275 A | 12/1997 | Bell et al. |
| 5,702,408 A | 12/1997 | Wales et al. |
| 5,704,534 A | 1/1998 | Huitema et al. |
| 5,713,505 A | 2/1998 | Huitema |
| 5,725,536 A | 3/1998 | Oberlin et al. |
| 5,749,828 A | 5/1998 | Solomon et al. |
| 5,766,196 A | 6/1998 | Griffiths |
| 5,766,205 A | 6/1998 | Zvenyatsky et al. |
| 5,772,578 A | 6/1998 | Heimberger et al. |
| 5,772,655 A | 6/1998 | Bauer et al. |
| 5,782,859 A | 7/1998 | Nicholas et al. |
| 5,791,231 A | 8/1998 | Cohn et al. |
| 5,792,135 A | 8/1998 | Madhani et al. |
| 5,794,834 A | 8/1998 | Hamblin et al. |
| 5,797,537 A | 8/1998 | Oberlin et al. |
| 5,807,235 A | 9/1998 | Heff |
| 5,807,241 A | 9/1998 | Heimberger |
| 5,807,376 A | 9/1998 | Viola et al. |
| 5,810,716 A | 9/1998 | Mukherjee et al. |
| 5,820,009 A | 10/1998 | Melling et al. |
| 5,823,066 A | 10/1998 | Huitema et al. |
| 5,827,323 A | 10/1998 | Klieman et al. |
| 5,833,692 A | 11/1998 | Cesarini et al. |
| 5,851,212 A | 12/1998 | Zirps et al. |
| 5,857,964 A | 1/1999 | Konstorum et al. |
| 5,860,995 A | 1/1999 | Berkelaar |
| 5,885,288 A | 3/1999 | Aust et al. |
| 5,899,914 A | 5/1999 | Zirps et al. |
| 5,916,146 A | 6/1999 | Allotta et al. |
| 5,921,956 A | 7/1999 | Grinberg et al. |
| 5,928,136 A | 7/1999 | Barry |
| 5,938,678 A | 8/1999 | Zirps et al. |
| 5,967,997 A | 10/1999 | Turturro et al. |
| 5,976,122 A | 11/1999 | Madhani et al. |
| 6,013,024 A | 1/2000 | Mitsuda et al. |
| 6,053,907 A | 4/2000 | Zirps |
| 6,063,098 A | 5/2000 | Houser et al. |
| 6,066,090 A | 5/2000 | Yoon |
| 6,077,287 A | 6/2000 | Taylor et al. |
| 6,126,633 A | 10/2000 | Kaji et al. |
| 6,139,508 A | 10/2000 | Simpson et al. |
| 6,174,280 B1 | 1/2001 | Oneda et al. |
| 6,179,776 B1 | 1/2001 | Adams et al. |
| 6,183,463 B1 | 2/2001 | Webster, Jr. |
| 6,203,494 B1 | 3/2001 | Moriyama |
| 6,248,062 B1 | 6/2001 | Adler et al. |
| 6,270,453 B1 | 8/2001 | Sakai |
| 6,371,425 B2 | 4/2002 | Fidler |
| 6,371,952 B1 | 4/2002 | Madhani et al. |

(56) References Cited

U.S. PATENT DOCUMENTS

| | | | |
|---|---|---|---|
| 6,408,889 B1 | 6/2002 | Komachi |
| 6,409,727 B1 | 6/2002 | Bales et al. |
| 6,443,973 B1 | 9/2002 | Whitman |
| 6,464,711 B1 | 10/2002 | Emans et al. |
| 6,482,149 B1 | 11/2002 | Torii |
| 6,491,626 B1 | 12/2002 | Stone et al. |
| 6,569,105 B1 | 5/2003 | Kortenbach et al. |
| 6,589,200 B1 | 7/2003 | Schwemberger et al. |
| 6,595,982 B2 | 7/2003 | Sekino et al. |
| 6,605,086 B2 | 8/2003 | Hayzelden et al. |
| 6,610,007 B2 | 8/2003 | Belson et al. |
| RE38,335 E | 11/2003 | Aust et al. |
| 6,641,528 B2 | 11/2003 | Torii |
| 6,652,508 B2 | 11/2003 | Griffin et al. |
| 6,656,195 B2 | 12/2003 | Peters et al. |
| 6,666,854 B1 | 12/2003 | Lange |
| 6,672,338 B1 | 1/2004 | Esashi et al. |
| 6,698,643 B2 | 3/2004 | Whitman |
| 6,716,207 B2 | 4/2004 | Farnholtz |
| 6,716,233 B1 | 4/2004 | Whitman |
| 6,726,700 B1 | 4/2004 | Levin |
| 6,743,239 B1 | 6/2004 | Kuehn et al. |
| 6,761,717 B2 | 7/2004 | Bales et al. |
| 6,786,382 B1 | 9/2004 | Hoffman |
| 6,793,622 B2 | 9/2004 | Konomura et al. |
| 6,800,056 B2 | 10/2004 | Tartaglia et al. |
| 6,814,728 B2 | 11/2004 | Ouchi et al. |
| 6,817,974 B2 | 11/2004 | Cooper et al. |
| 6,837,846 B2 | 1/2005 | Jaffe et al. |
| 6,846,307 B2 | 1/2005 | Whitman et al. |
| 6,858,005 B2 | 2/2005 | Ohline et al. |
| 6,863,668 B2 | 3/2005 | Gillespie et al. |
| 6,887,195 B1 | 5/2005 | Pilvisto |
| 6,902,528 B1 | 6/2005 | Garibaldi et al. |
| 6,936,061 B2 | 8/2005 | Sasaki |
| 6,951,537 B2 | 10/2005 | Hirata |
| 6,964,363 B2 | 11/2005 | Wales et al. |
| 6,981,628 B2 | 1/2006 | Wales |
| 6,984,203 B2 | 1/2006 | Tartaglia et al. |
| 6,991,627 B2 | 1/2006 | Madhani et al. |
| 6,994,716 B2 | 2/2006 | Jinno et al. |
| 7,043,338 B2 | 5/2006 | Jinno |
| 7,044,245 B2 | 5/2006 | Anhalt et al. |
| RE39,152 E | 6/2006 | Aust et al. |
| 7,055,731 B2 | 6/2006 | Shelton, IV et al. |
| 7,077,823 B2 | 7/2006 | McDaniel |
| 7,087,071 B2 | 8/2006 | Nicholas et al. |
| 7,090,637 B2 | 8/2006 | Danitz et al. |
| 7,111,769 B2 | 9/2006 | Wales et al. |
| 7,115,183 B2 | 10/2006 | Larson et al. |
| 7,135,030 B2 | 11/2006 | Schwemberger et al. |
| 7,147,650 B2 | 12/2006 | Lee |
| 7,213,736 B2 | 5/2007 | Wales et al. |
| 7,276,067 B2 | 10/2007 | Bales et al. |
| 7,316,681 B2 | 1/2008 | Madhani et al. |
| 7,320,700 B2 | 1/2008 | Cooper et al. |
| 7,326,176 B2 | 2/2008 | Machiya et al. |
| 7,338,513 B2 | 3/2008 | Lee et al. |
| 7,364,582 B2 | 4/2008 | Lee |
| 7,402,151 B2 | 7/2008 | Rosenman et al. |
| 7,410,483 B2 | 8/2008 | Danitz et al. |
| 7,419,477 B2 | 9/2008 | Simpson et al. |
| 7,431,720 B2 | 10/2008 | Pendekanti et al. |
| 7,455,208 B2 | 11/2008 | Wales et al. |
| D583,051 S | 12/2008 | Lee et al. |
| 7,481,348 B2 | 1/2009 | Marczyk |
| 7,481,824 B2 | 1/2009 | Boudreaux et al. |
| 7,553,275 B2 | 6/2009 | Padget et al. |
| 7,608,375 B2 | 10/2009 | Miyakawa |
| 7,615,066 B2 | 11/2009 | Danitz et al. |
| 7,615,067 B2 | 11/2009 | Lee et al. |
| 7,648,519 B2 | 1/2010 | Lee et al. |
| 7,654,431 B2 | 2/2010 | Hueil et al. |
| 7,662,091 B2 | 2/2010 | Bagley et al. |
| 7,670,284 B2 | 3/2010 | Padget et al. |
| 7,670,334 B2 | 3/2010 | Hueil et al. |
| 7,673,780 B2 | 3/2010 | Shelton, IV et al. |
| 7,678,117 B2 | 3/2010 | Hinman et al. |
| 7,682,307 B2 | 3/2010 | Danitz et al. |
| 7,686,826 B2 | 3/2010 | Lee et al. |
| 2003/0083550 A1 | 5/2003 | Miyagi |
| 2004/0034348 A1 | 2/2004 | Rashidi |
| 2004/0236316 A1 | 11/2004 | Danitz et al. |
| 2005/0033319 A1 | 2/2005 | Gambale et al. |
| 2005/0107667 A1 | 5/2005 | Danitz et al. |
| 2005/0187575 A1 | 8/2005 | Hallbeck et al. |
| 2005/0222601 A1 | 10/2005 | Erhard |
| 2005/0251112 A1 | 11/2005 | Danitz et al. |
| 2005/0270385 A1 | 12/2005 | Shioya et al. |
| 2005/0273084 A1 | 12/2005 | Hinman et al. |
| 2006/0025810 A1 | 2/2006 | Shelton, IV |
| 2006/0025811 A1 | 2/2006 | Shelton, IV |
| 2006/0025813 A1 | 2/2006 | Shelton et al. |
| 2006/0047302 A1 | 3/2006 | Ortiz et al. |
| 2006/0094931 A1 | 5/2006 | Danitz et al. |
| 2006/0095074 A1 | 5/2006 | Lee et al. |
| 2006/0111209 A1* | 5/2006 | Hinman et al. ............... 474/206 |
| 2006/0111210 A1 | 5/2006 | Hinman et al. |
| 2006/0111615 A1 | 5/2006 | Danitz et al. |
| 2006/0111616 A1 | 5/2006 | Danitz |
| 2006/0135961 A1 | 6/2006 | Rosenman et al. |
| 2006/0190032 A1 | 8/2006 | Wales |
| 2006/0201130 A1 | 9/2006 | Danitz |
| 2007/0021737 A1 | 1/2007 | Lee |
| 2007/0135803 A1 | 6/2007 | Belson |
| 2007/0161291 A1 | 7/2007 | Swinehart et al. |
| 2007/0161857 A1 | 7/2007 | Durant et al. |
| 2007/0250110 A1 | 10/2007 | Lu et al. |
| 2007/0250113 A1 | 10/2007 | Hegeman et al. |
| 2007/0276430 A1 | 11/2007 | Lee et al. |
| 2007/0282371 A1 | 12/2007 | Lee et al. |
| 2007/0287993 A1 | 12/2007 | Hinman et al. |
| 2008/0015631 A1 | 1/2008 | Lee et al. |
| 2008/0046000 A1 | 2/2008 | Lee et al. |
| 2008/0065098 A1 | 3/2008 | Larkin |
| 2008/0154288 A1 | 6/2008 | Belson |
| 2008/0221392 A1 | 9/2008 | Jorgensen |
| 2008/0255420 A1 | 10/2008 | Lee et al. |
| 2008/0255421 A1 | 10/2008 | Hegeman et al. |
| 2008/0255588 A1 | 10/2008 | Hinman |
| 2008/0255608 A1 | 10/2008 | Hinman et al. |
| 2008/0262492 A1 | 10/2008 | Lee |
| 2008/0262537 A1 | 10/2008 | Lee et al. |
| 2008/0262538 A1 | 10/2008 | Danitz et al. |
| 2008/0269727 A1 | 10/2008 | Lee |
| 2008/0287918 A1 | 11/2008 | Rosenman et al. |
| 2008/0294191 A1 | 11/2008 | Lee |
| 2009/0023995 A1 | 1/2009 | Lee |
| 2009/0099420 A1 | 4/2009 | Woodley et al. |
| 2009/0171147 A1 | 7/2009 | Lee et al. |
| 2009/0171159 A1 | 7/2009 | Jorgensen et al. |
| 2009/0187185 A1 | 7/2009 | Lyons et al. |
| 2009/0192498 A1 | 7/2009 | Andrew et al. |
| 2009/0216083 A1 | 8/2009 | Durant et al. |
| 2009/0299143 A1* | 12/2009 | Conlon et al. ............... 600/153 |
| 2009/0306658 A1 | 12/2009 | Nobis et al. |
| 2009/0320637 A1 | 12/2009 | Doyle et al. |
| 2010/0041945 A1 | 2/2010 | Isbell, Jr. |
| 2010/0243840 A1 | 9/2010 | Nesper et al. |
| 2011/0022078 A1* | 1/2011 | Hinman ...................... 606/206 |
| 2012/0083770 A1* | 4/2012 | Paik et al. ................... 606/1 |

FOREIGN PATENT DOCUMENTS

| | | |
|---|---|---|
| EP | 2 044 888 A3 | 7/2009 |
| WO | 99/15090 A1 | 4/1999 |
| WO | 00/67834 A1 | 11/2000 |
| WO | WO 2010/112608 A1 | 10/2010 |

* cited by examiner

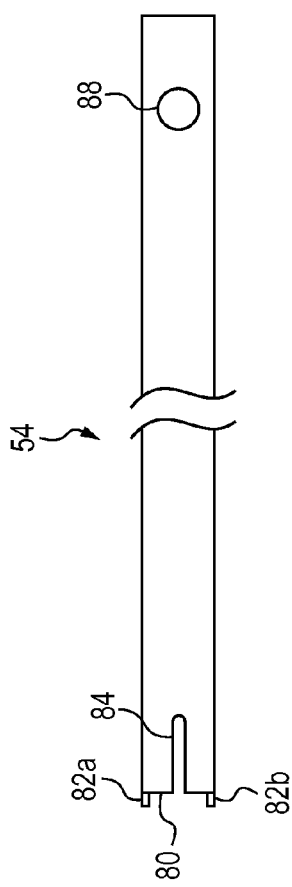
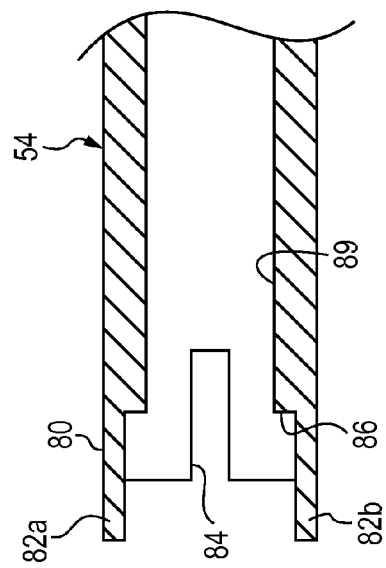
FIG. 2A
FIG. 2B

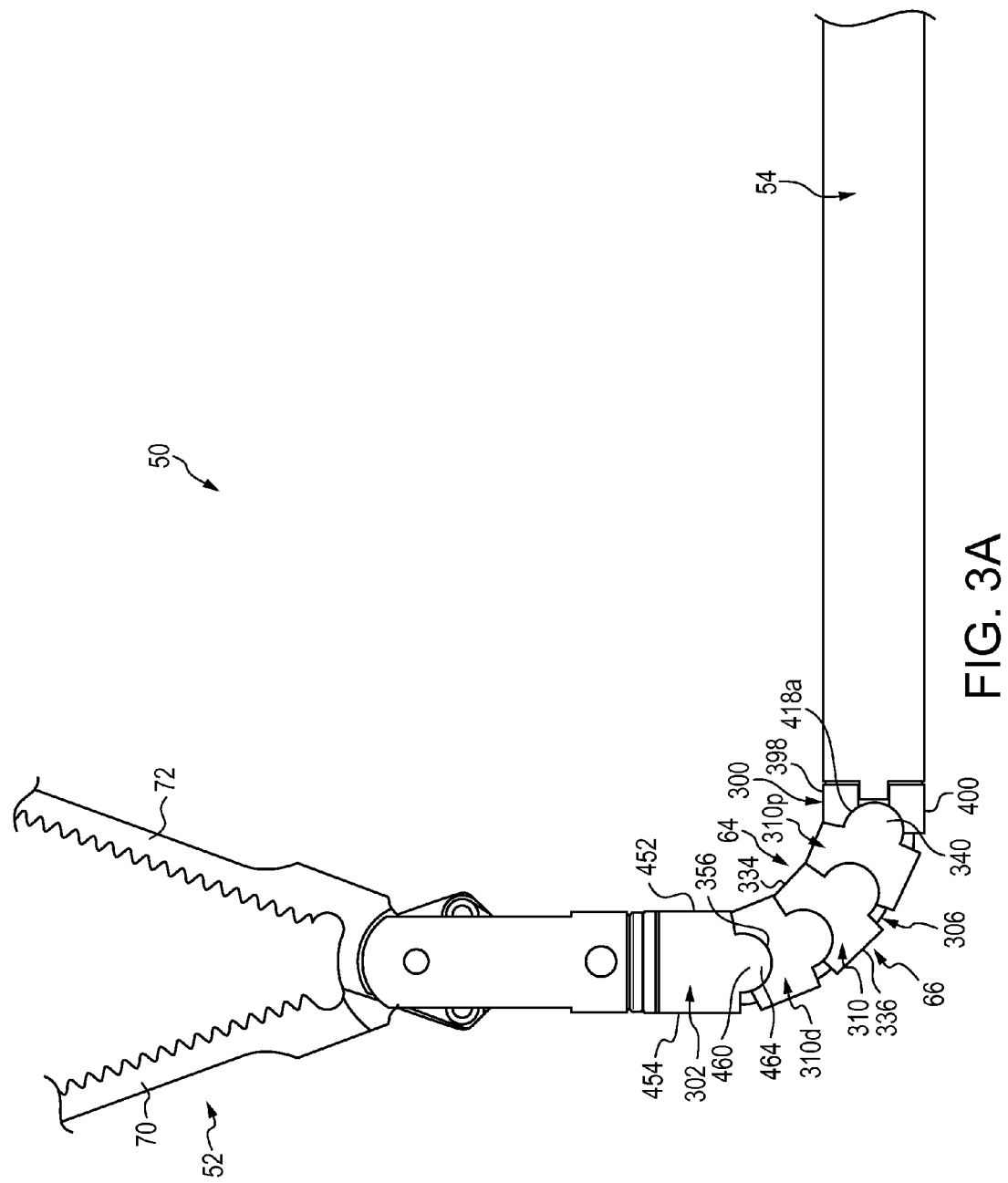

WRIST ASSEMBLY FOR ARTICULATING LAPAROSCOPIC SURGICAL INSTRUMENTS

BACKGROUND

The present disclosure relates to articulating laparoscopic surgical instruments. More particularly, it relates to articulating laparoscopic surgical instruments having a low profile wrist assembly providing user control over operation and spatial positioning of an end effector carried by the instrument so as to be useful in performing, for example, single incision laparoscopic procedures.

There is a growing trend in laparoscopic surgery to be as minimally invasive as possible. This has pushed surgeons to perform procedures with fewer and smaller incisions. With more recent protocols, only one incision is made (in the umbilicus) through which all of the instrumentation and even the camera are inserted. While highly promising, this technique presents many obstacles including lack of triangulation, instrument reach, handle clashing, etc.

Various articulating laparoscopic surgical instruments have been developed in an attempt to address one or more of the above concerns. In general terms, an articulating laparoscopic surgical instrument includes an elongated shaft carrying an end effector (or "working end") at the shaft's distal end. The end effector can assume various forms, such as scissors, graspers, needle holders, dissectors, clamps, electrocautery implements, electrode probes, etc. A wrist portion of the instrument (typically proximate the end effector) can be caused to deflect or bend. A handle at the proximal end of the shaft affords user control over the end effector and the articulating wrist. When employed with laparoscopic procedures, articulating instruments allow the surgeon to regain triangulation during single port surgery by aiming the shaft of the surgical instrument slightly away and then curving the working end (or end effector) back toward the operative site. In addition, their longer lengths provide the surgeon the reach needed for organs further away from the umbilicus. Further, their low profile handles minimize handle clashing at the entrance site.

To be truly viable, the articulating laparoscopic instrument should afford user control, via actuators along the instrument's handle, over operation of the end effector, rotation of the end effector, and articulation of the wrist or shaft. The mechanisms necessary to provide these multiple control features at the small scales associated with laparoscopic instrumentation are inherently intricate and dramatically increase the instrument's cost. In this regard, surgeons desire the ability to control, via actuators carried on or near the handle, all three movements (i.e., end effector operation, end effector rotation, and shaft articulation) independent of one another. An additional control feature provided with some laparoscopic instruments is an ability to rotate the outer shaft (thus re-orienting a spatial of location of any bend formed along the wrist or shaft). These requirements give rise to much technical difficulty, especially when accounting for the independent transmission of torque (for end effector rotation) from the handle actuator and through or around a bend in the wrist or shaft. While existing articulating laparoscopic surgical instruments may provide one or more of these features, they are limited to one-time use or are otherwise disposable because their design does not allow for proper cleaning and sterilization. Nor are they robust enough to stand up to repeated use. Due to the high cost, single-use nature of existing articulating laparoscopic instruments, a caregiver may unfortunately decide against purchasing or using such instruments. As a result, the single incision laparoscopic surgical procedures performed by the caregiver will be more complicated or even avoided.

In light of the above, a need exists for improved articulating laparoscopic instruments having a wrist joint assembly that facilitates desired surgeon control over instrument operation, articulation, and rotation.

SUMMARY

Some aspects of the present disclosure relate to an articulating surgical instrument including a handle, an outer shaft, an end effector, and a wrist assembly. The outer shaft extends from the handle to a shaft end. The wrist assembly connects the end effector to the shaft end, and includes a torque mechanism and an articulation mechanism. In some embodiments, the wrist assembly further comprises an end effector operation mechanism. With optional constructions in which the end effector includes two moveably connected bodies, the end effector operation mechanism includes a rod extending through the shaft and coupled to the end effector such that longitudinal movement of the rod relative to the end effector causes the first body to move relative to the second body. The torque mechanism includes a plurality of links disposed between the shaft and the effector. The links are collectively adapted to transfer a rotational force from a proximal-most link to the effector. Finally, the articulation mechanism includes a plurality of articulation members disposed between the shaft and the end effector to collectively define a deflection section. In this regard, the articulation mechanism is adapted to spatially articulate the end effector relative to the shaft end. The wrist assembly is configured such that the links articulate with articulation of the deflection section, and the links rotate independent of the articulation members. With the above construction, the wrist assembly can have a low profile while providing a user with the ability to operate and rotate the effector, and to articulate the effector relative to the outer shaft. In some embodiments, each of the links is seated within a corresponding one of articulation members in a manner permitting the link to rotate relative to the corresponding articulation member. Further, cable segments provided with the articulation mechanism interconnect the articulation members, with tensioning of the cable segments bringing the articulation members into operative connection with one another, as well as bringing the links into operative connection to one another. In an optional cleaning mode provided with some embodiments of the surgical instrument, sufficient slack is created in the cable segments to permit the articulation members to be physically separated from one another, and the links to be physically separated from one another. In other embodiments, each of the links defines a male end portion and a female end portion, with the male end portion forming a polygonal ball head and the female end portion forming a corresponding, polygonal socket.

Other aspects of the present disclosure relate to an articulating laparoscopic surgical instrument including the handle, outer shaft, end effector, and wrist assembly components described above. The wrist assembly is configured such that during actuation of the optional end effector operation mechanism in operating the end effector, the rod slides longitudinally relative to the links and the articulation members. During actuation of the torque mechanism in rotating the end effector, the links rotate relative to the articulation members and the optional rod (where provided). Finally, during actuation of the articulation mechanism in spatially moving the end effector relative to the shaft end, a bending force generated by the deflection of the assembly is applied to the plurality of links and the optional rod (where provided). Thus, the wrist assembly provides for independent operation of each of the end effector operation mechanism, torque mechanism, and articulation mechanism.

BRIEF DESCRIPTION OF THE DRAWINGS

FIG. 2A is a side view of an outer shaft component useful with the surgical instrument of FIG. 1;

FIG. 2B is a cross-sectional view of a portion of the outer shaft of FIG. 2A;

FIG. 3A is an enlarged, top plan view of a portion of the surgical instrument of FIG. 1, illustrating a distal region of a wrist assembly useful with the instrument, including a deflection section in a curved or articulated state;

DETAILED DESCRIPTION

Figure 1:
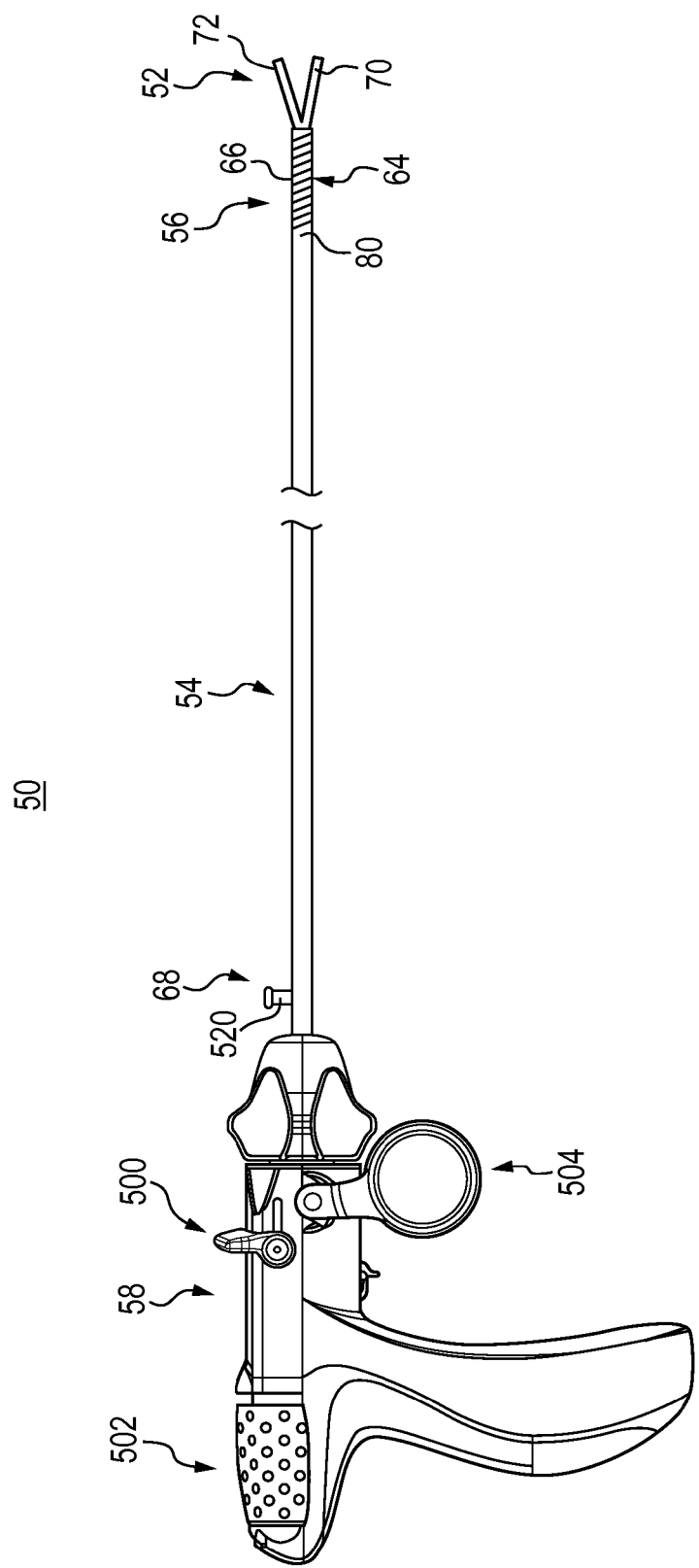
FIG. 1 is a side view of a surgical instrument in accordance with principles of the present disclosure.

One embodiment of an articulating laparoscopic surgical instrument 50 in accordance with principles of the present disclosure is shown in FIG. 1. The surgical instrument 50 includes an end effector 52, an outer shaft 54, a wrist assembly 56, and a handle assembly 58. Details on the various components are provided below. In general terms, however, the shaft 54 extends from the handle assembly 58 and maintains or is connected to the end effector 52 by the wrist assembly 56. While primarily hidden in the view of FIG. 1, the wrist assembly 56 includes in some embodiments an end effector operation mechanism 60 (hidden in FIG. 1, but shown, for example, in FIG. 4A), a torque mechanism 62 (hidden in FIG. 1, but shown, for example, in FIG. 4A), and an articulation mechanism 64 (referenced generally). Each of the mechanisms 60-64 are described below, and independently facilitate operation of the end effector 52, rotation of the end effector 52 relative to the shaft 54, and articulation of a deflection section 66 component of the articulation mechanism 64. In some embodiments, the instrument 50 further includes or forms a flush port assembly 68 through which internal cleaning and sterilization of portions of the instrument 50 (e.g., a lumen of the shaft 54) can be performed. Thus, in some embodiments, not only does the instrument 50 provide a user with all operational control desired for single incision laparoscopic procedures (e.g., end effector operation, rotation, and articulation), but also is reusable.

The end effector 52 can assume various forms useful with laparoscopic surgical procedures, such as scissors, grasper, clamp, dissector, needle holder, electrocautery implement, electrode probe, etc. In more general terms, the end effector 52 can include first and second bodies 70, 72 as shown, with at least the first body 70 being moveably coupled relative to the second body 72. This movable coupling can be effectuated in various forms, such as by a pinned or pivoting interface, a cammed interface, various linkages, etc., as are known to those of skill in the art. With other end effector constructions envisioned by the present disclosure, the end effector 52 consists of only a single primary body that does not move during operation thereof (e.g., an electrocautery implement, electrode probe, etc.). Regardless, the end effector 52 is configured for connection with one or more components of the end effector operation mechanism 60 in a manner that facilitates operation of the end effector 52 (e.g., user-caused and controlled spatial arrangement of the first body 70 relative to the second body 72, user-prompted energization of an electrocautery probe, etc.). In light of the wide variety of different end effector constructions implicated by the surgical instruments of the present disclosure, "operation" of the end effector is in reference to the movement(s) or other functions conventionally associated with the particular end effector design. Thus, "operation" of a scissors, grasper, or clamp-type end effector includes opening and closing of two opposing jaws relative to one another; "operation" of an electrode probe includes delivery of energy to (or receiving a signal from) the probe; etc. Other types of end effectors entail differing movements, and the present disclosure is not limited to any particular end effector design or corresponding operative movements.

The shaft 54 can also assume various forms appropriate for delivery through a conventional trocar (e.g., the shaft 54 has a maximum outer diameter of not more than 5.5 mm in some embodiments), and is generally tubular in shape. The tubular shaft 54 extends distally from the handle assembly 58 and terminates at a shaft distal end 80. As shown, portions of the wrist assembly 56 extend from the shaft end distal 80 including, for example, the deflection section 66. The shaft 54 is relatively rigid, whereas the deflection section 66 is configured to reversibly articulate/bend and straighten in response to an applied force or tension as described below. As a point of reference, the term "longitudinal" as used throughout the present disclosure is in reference to or based upon the linear central axis of the shaft 54.

In some embodiments, the outer shaft 54 can incorporate one or more features at the distal end 80 that facilitate mounting with corresponding component(s) of the wrist assembly 56. As shown in FIGS. 2A and 2B, for example, the outer shaft 54 can form or carry opposing tines 82a, 82b at the distal end 80, along with opposing slots 84 (one of which is visible in FIGS. 2A and 2B). The tines 82a, 82b are configured for connection to a wrist assembly component, with a wall thickness of the shaft 54 being reduced adjacent the distal end 80 (e.g., a counter-bore is formed along an inner diameter of the shaft 54) to define a stop surface 86 for seated engagement with wrist assembly component. The slots 84 facilitate passage of wrist assembly cable segments as described below. A wide variety of other mounting techniques are also acceptable that may or may not include the tines 82a, 82b and/or the slots 84. Finally, FIG. 2A shows an optional bore 88 formed in the shaft 54. Where provided, the bore 88 is aligned with the flush port assembly 68 (FIG. 1) for delivery of cleaning liquid into a lumen 89 of the shaft 54.

Figure 3B:
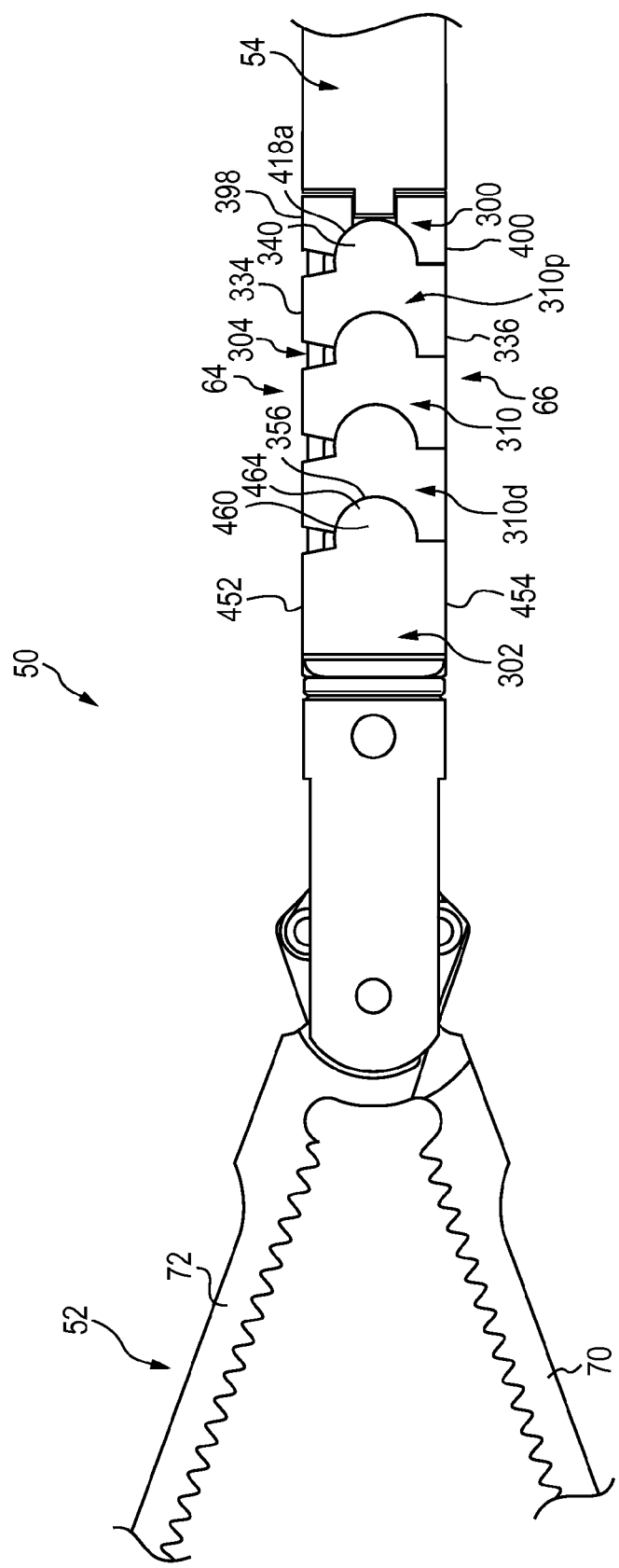
FIG. 3B is the enlarged top plan view of FIG. 3A with the deflection section in a straightened state.
Figure 4A:
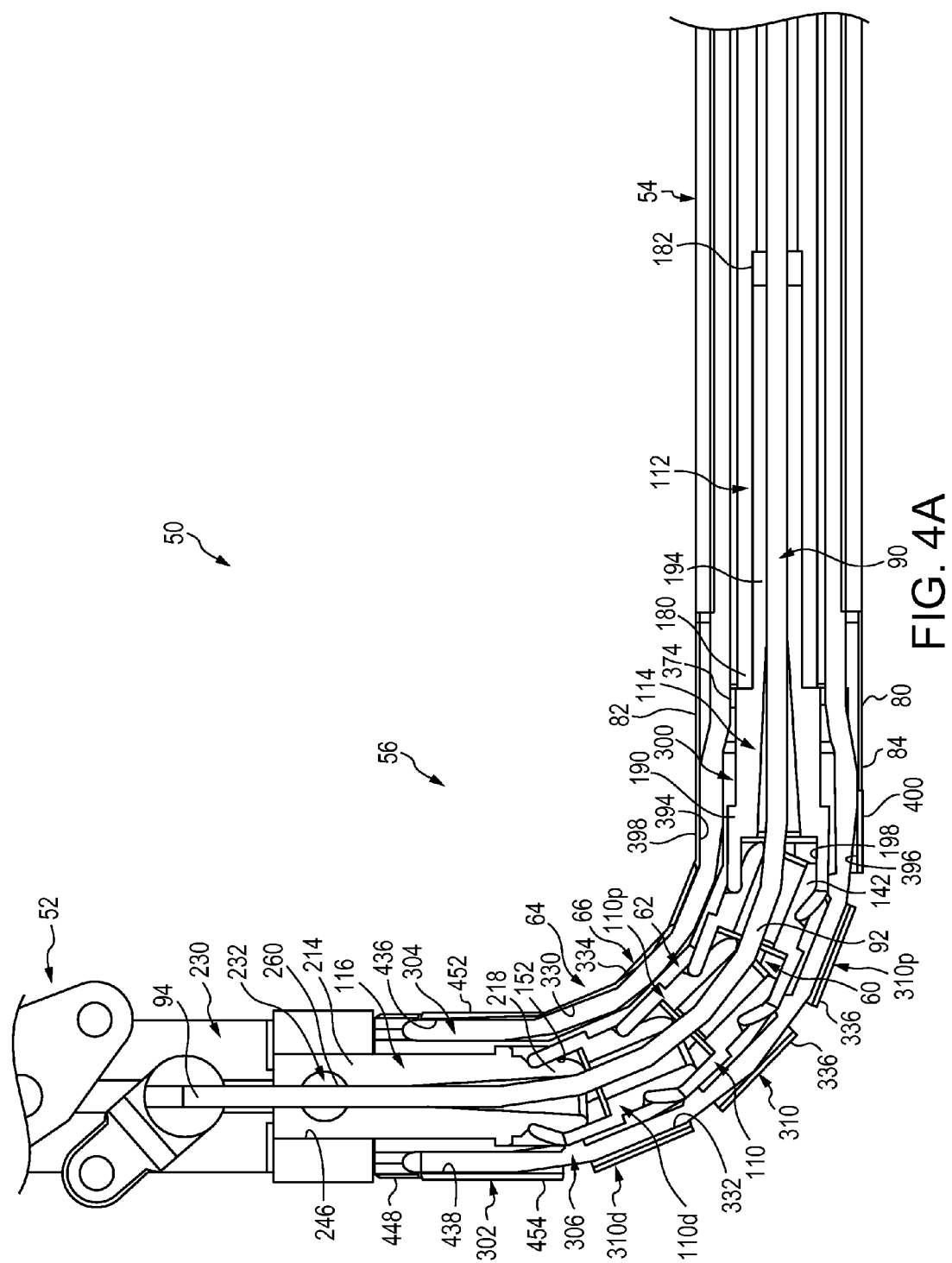
FIG. 4A is a cross-sectional view of the instrument portion of FIG. 3A.
Figure 4B:
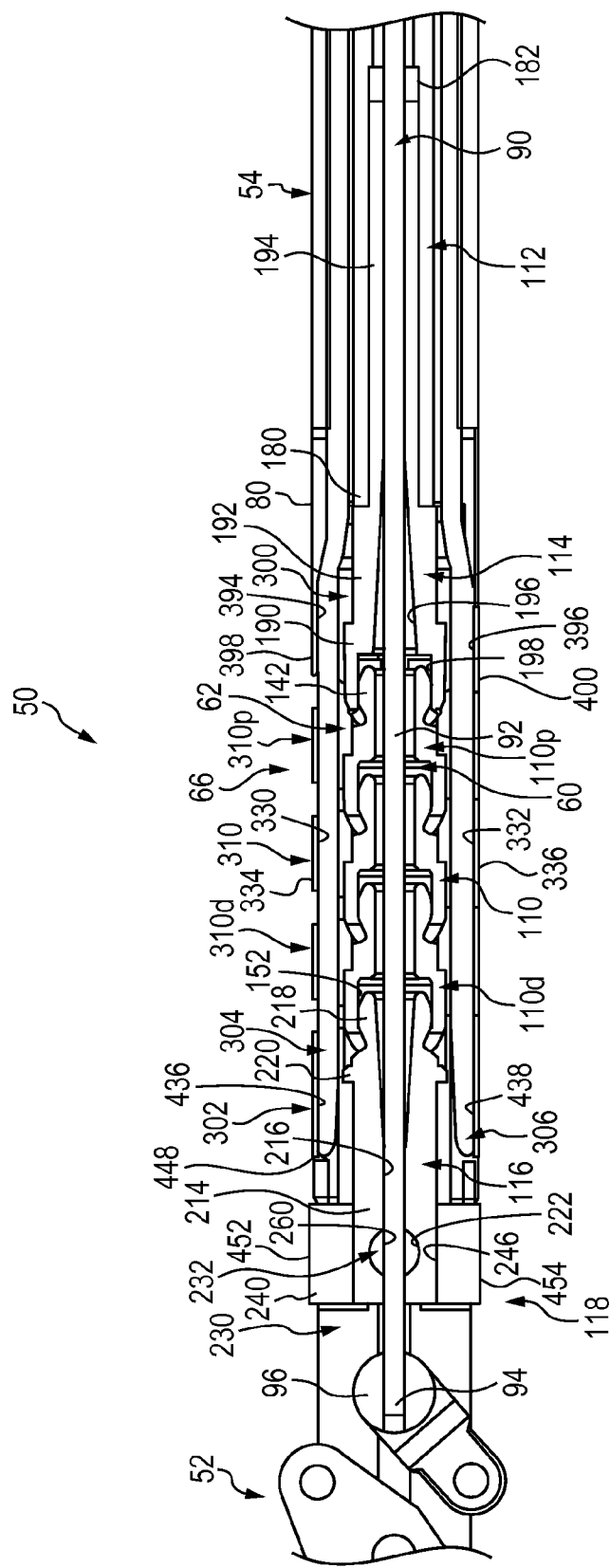
FIG. 4B is a cross-sectional view of the instrument portion of FIG. 3B.

FIGS. 3A-4B illustrate a distal region of the surgical instrument 50, showing portions of the wrist assembly 56 in greater detail. In particular, FIGS. 3A and 3B are top plan views of the distal region in a curved or articulated (FIG. 3A) and straightened (FIG. 3B) arrangement of the deflection section 66. FIGS. 4A and 4B are cross-sectional views of the arrangements of FIGS. 3A and 3B, respectively. Included in the views are components of the end effector operation mechanism 60, the torque mechanism 62, and the articulation mechanism 64, relative to the end effector 52 and the shaft distal end 80. As a point of reference, the mechanisms 60-64 each extend to, and/or include additional components at, a proximal region of the surgical instrument (e.g., at the handle assembly 58 (FIG. 1)) to facilitate user-controlled actuation of each mechanism 60-64. The distal region portions of each of the mechanisms 60-64 are described below, followed by a description of connections of the mechanisms 60-64 at the handle assembly 58.

End Effector Operation Mechanism 60

The end effector operation mechanism 60 is best seen in FIGS. 4A and 4B, and includes a rod 90 that is received within the shaft 54, and extends distally from the shaft distal end 80. A distal portion 92 of the rod 90 is disposed within the deflection section 66, and terminates at a distal end 94 that is coupled to the end effector 52. At least the distal portion 92 of the rod 90 exhibits sufficient flexibility to bend/straighten in response to corresponding forces applied by the deflection section 66 (it being understood that in some embodiments, articulation forces generated by the deflection section 66 are transferred to the rod 90 via components of the torque mechanism 62 as described below). The distal portion 92 thus follows the shape or curvature defined by the deflection section 66, and will not permanently deform with repeated bending and straightening. For example, the distal portion 92 is shown to have been forced to a curved or bent shape by the deflection section 66 in the arrangement of FIG. 4A; under circumstances where the deflection section 66 is caused to assume a more straightened shape as in FIG. 4B, the rod distal portion 92 is forced to and will readily assume a corresponding shape.

The rod 90 can be homogenously formed of a durable yet flexible material such as Nitinol™ or other material(s) that is robustly capable of repeated bending/straightening along the distal portion 92. In other constructions, the rod 90 can consist of two (or more) discrete materials, such as a proximal portion formed of stainless steel and the distal portion 92 (or section of the distal portion 92 otherwise disposed within the deflection section 66) formed of Nitinol. The durable yet flexible construction of the rod 90 is sufficient to not only accommodate the articulation/bending described above, but also the axial compression/extension forces encountered during use of the instrument 50. For example, the rod 90 can be capable of maintaining its structural integrity in the presence of a tension force on the order of 150 lbf and a compression force on the order of 30 lbf. Further, material(s) selected for the rod 90 are optionally able to maintain their structural integrity when subjected to repeated sterilization.

Figure 5A:
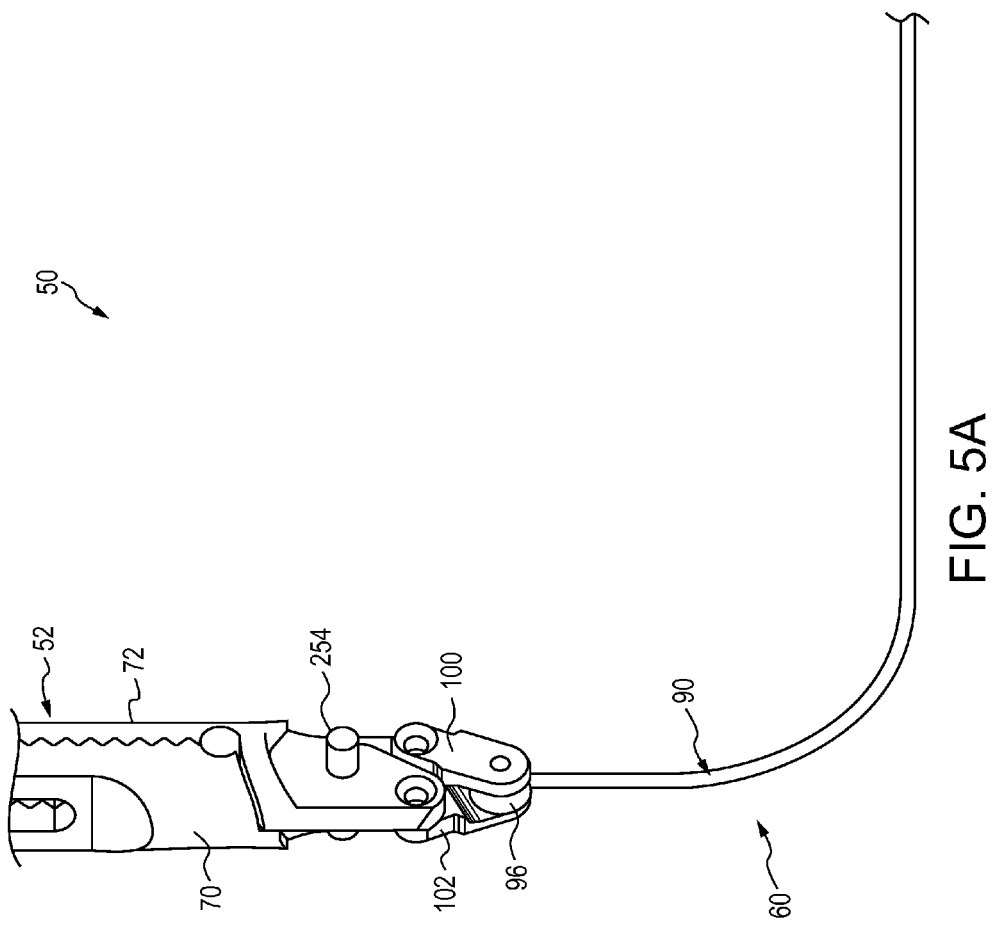
FIG. 5A is a perspective view of portions of the wrist assembly of FIG. 4A, including components of an end effector operation mechanism useful with the wrist assembly.
Figure 5B:
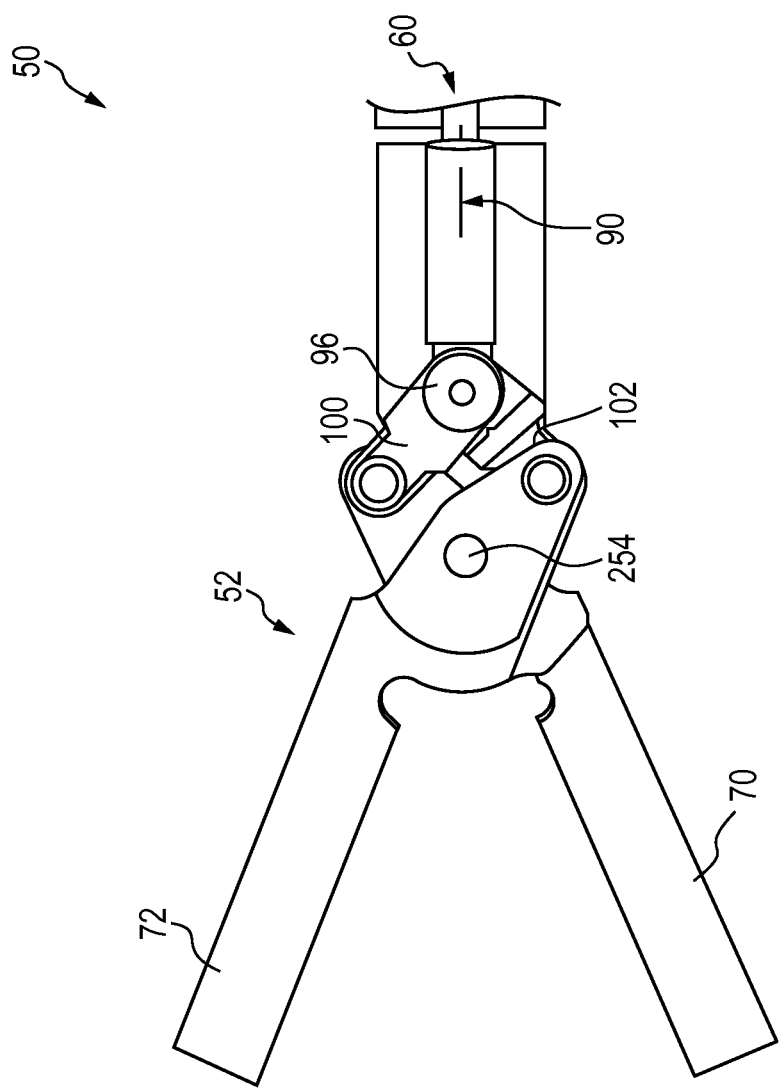
FIG. 5B is a side view of a portion of the instrument of FIG. 4A, illustrating a relationship between the end effector and the end effector operation mechanism.

Coupling between the distal end 94 and the end effector 52 can be achieved in various manners, and is more generally described as establishing a push/pull type link with the end effector 52 in some embodiments. With constructions in which the end effector 52 includes two bodies 70, 72 that can move relative to one another, because the end effector 52 is effectively longitudinally fixed relative to the shaft 54 and because the rod 90 can longitudinally slide relative to the shaft 54, longitudinal movement of the rod 90 relative to the end effector 52 causes the first body 70 to move relative to the second body 72. With additional reference to FIGS. 5A and 5B, the end effector operation mechanism 62 can include an adaptor 96 that pivotably couples the distal end 94 with arms 100, 102. The arms 100, 102 can alternatively be viewed as being components of the end effector 52. Regardless, the arms 100, 102 are connected to a corresponding one of the end effector bodies 70, 72. With the one example end effector construction shown, the arms 100, 102 are pivotably coupled to the corresponding end effector body 70, 72. Distal or longitudinally forward movement (i.e., pushing force) of the rod 90 causes the bodies 70, 72 to pivot open relative to one another (i.e., transition from the arrangement of FIG. 5A to that of FIG. 5B), whereas proximal or longitudinally rearward movement (i.e., pulling force) of the rod 90 causes the bodies 70, 72 to close (i.e., transition from the arrangement of FIG. 5B to that of FIG. 5A). It will be understood that the end effector 52 can incorporate a variety of other mechanisms or components that are operable in response to push/pull movement of the rod 90 (e.g., camming interface, etc.). Even further, with non-moving end effector constructions (e.g., electrode probe), a push/pull-type relationship with the rod 90 may be unnecessary, such that the rod 90 is directly mounted to the end effector 52.

Torque Mechanism 62

Returning to FIGS. 4A and 4B, the torque mechanism 62 includes a plurality of links 110, a torque shaft 112, a proximal drive body 114, a distal drive body 116, and a coupling assembly 118 (referenced generally). The plurality of links 110 are consecutively arranged and the proximal drive body 114 connects the torque shaft 112 to the proximal-most link 110p. Similarly, the distal drive body 116 connects the distal-most link 110d to the coupling assembly 118 that in turn is connected to the end effector 52. With this construction, rotation of the end effector 52 can be effectuated via a user-applied torque or rotational force at the torque shaft 112, with the plurality of links 110 accommodating and transferring the torque along any bend dictated by the deflection section 66.

The torque mechanism 62 is depicted as including three of the links 110; in other embodiments, a greater or lesser number of the links 110 are provided. The links 110 are discrete from one another, and are constructed such that upon final assembly, successive ones of the links 110 are rotationally locked to one another in a manner that permits adjacent links 110 to pivot relative to one another while maintaining the rotational lock.

The links 110 can be identical, with FIGS. 6A-6E illustrating one of the links 110 in greater detail. The link 110 is an integral body formed of a hardened, surgically safe material (e.g., surgical grade stainless steel) that optionally is able to maintain its structural integrity with subjected to repeated sterilization. The link 110 is shaped to define a male end portion 130, an intermediate portion 132, a female end portion 134, and a central bore 136 extending along a longitudinal axis L of the link 110. The central bore 136 is open at opposing, first and second ends 138, 140 of the link 110.

Figure 6A:
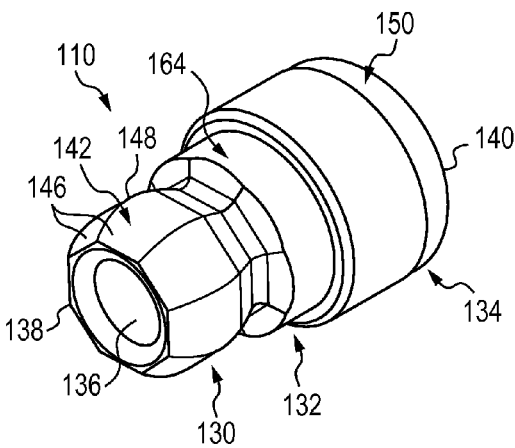
FIG. 6A is a perspective view of a link component of a torque mechanism useful with the wrist assembly of FIG. 4A.
Figure 6B:
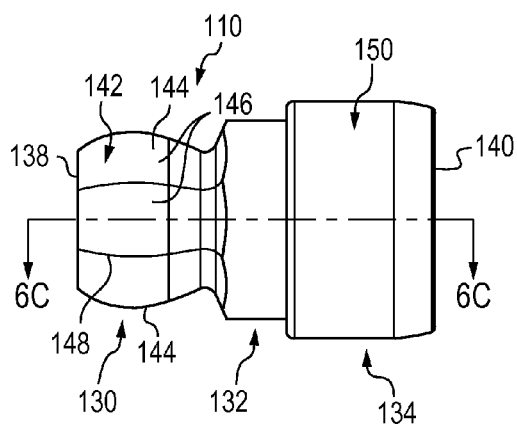
FIG. 6B is a side view of the link of FIG. 6A.
Figure 6C:
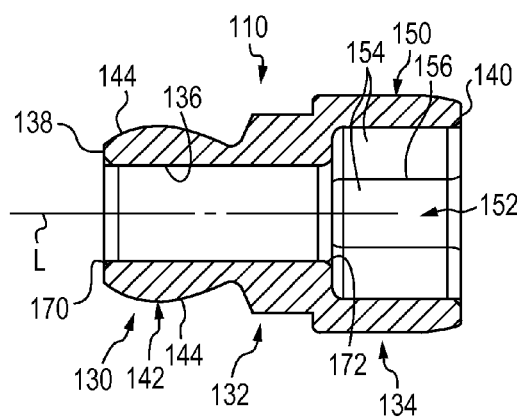
FIG. 6C is a cross-sectional view of the link of FIG. 6B, taken along the line 6C-6C.
Figure 6D:
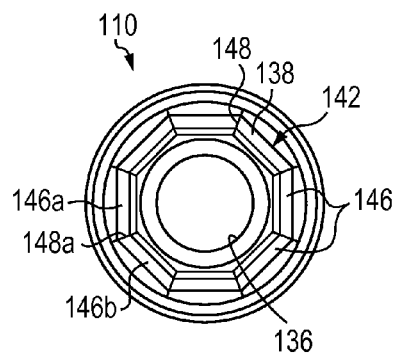
FIG. 6D is an end view of the link of FIG. 6A.
Figure 6E:
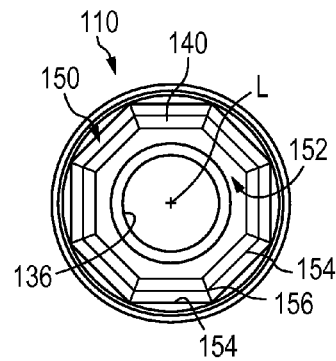
FIG. 6E is an opposite end view of the link of FIG. 6A.

The male end portion 130 and the female end portion 134 are generally configured to provide corresponding, mating features that facilitate pivotable, rotationally locked connection between successive links 110 (e.g., the male end portion 130 of one link is matingly-received within the female end portion 134 of a consecutively-next link). With this in mind, an exterior of the male end portion 130 forms a polygonal ball head 142 in extension from the first end 138 toward the intermediate portion 132. The ball head 142 has a generally spherical shape, initially expanding in diameter from the first end 138, then contracting in diameter toward the intermediate portion 132. As best shown in FIGS. 6B and 6C, relative to a plane passing through the longitudinal axis L, the ball head 142 has curved lateral edges 144. As best shown in FIG. 6D, relative to a plane perpendicular to the longitudinal axis L, the ball head 142 has a polygonal shaped cross-section. Stated otherwise, and with reference to FIGS. 6A, 6B, and 6D, the polygonal shape of the ball head 142 is generated by flats 146, with adjacent ones of the flats 146 forming a corner 148 (e.g., as identified in the view of FIG. 6D, a corner 148a is formed at an intersection between first and second flats 146a, 146b). However, each of the flats 146 (as well as the corners 148) has a convex curvature in a direction of the longitudinal axis L.

While the ball head 142 is shown as having an octagonal shape (i.e., eight of the flats 146 and eight of the corners 148), other polygonal shapes are also acceptable. For example, the ball head 142 shape can be hexagonal, decagonal, etc.

The female end portion 134 extends from the second end 140 toward the intermediate portion 132 and forms or defines a polygonal socket head 150. In particular, the socket head 150 provides a receptacle 152 (best shown in FIG. 6C) that is contiguous with the central bore 136 and has a polygonal shape corresponding with that of the ball head 142 (e.g., where the ball head 142 is octagonal in shape, the receptacle 152 is also octagonal). As reflected in FIGS. 6C and 6E, the polygonal shape of the receptacle 152 is defined by or includes flattened surfaces 154, adjacent ones of which intersect at a corner 156. The number of flattened surfaces 154 corresponds with the number of flats 146 provided on the ball head 142, but the flattened surfaces 154 do not have the convexly-curved shape in longitudinal cross-section. A diameter of the receptacle 152 corresponds with a maximum outer diameter of the ball head 142.

Figure 7A:
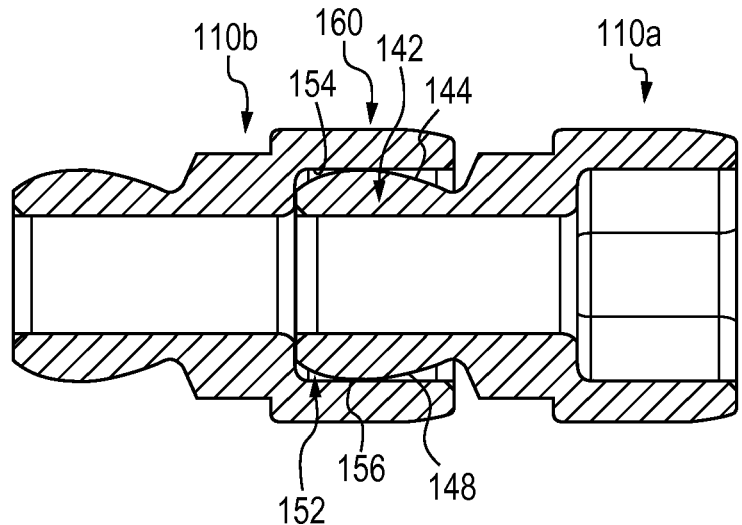
FIGS. 7A-7C are cross-sectional views illustrating coupling between two of the links of FIG. 6A.
Figure 7B:
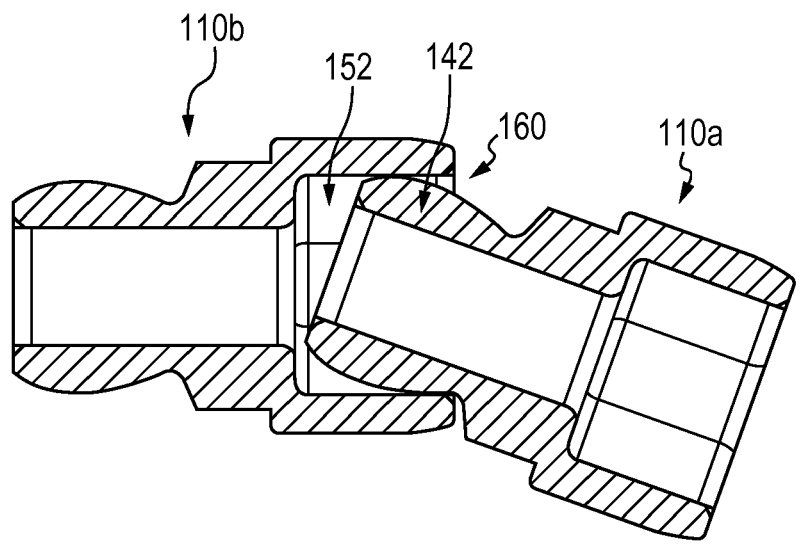

The corresponding constructions of the male and female end portions 130, 134 facilitates a pivotable yet rotationally locked interface between two of the links 110. For example, FIG. 7A illustrate a first one of the links 110a connected to a second one of the links 110b. The ball head 142 of the first link 110a is received within the receptacle 152 of the second link 110b. The ball head corners 148 of the first link 110a nest within the receptacle corners 156 of the second link 110b. Thus, a link interface 160 (referenced generally) is established at which rotation of the first link 110a is transferred to the second link 110b (and vice-versa). The link interface 160 permits the first link 110a to pivot relative to the second link 110b (and vice-versa), with the ball head curved edges 148 of the first link 110a traversing along a corresponding one of the receptacle flattened surfaces 154 of the second link 110b. Thus, and as shown in FIG. 7B, the first and second links 110a, 110b can be pivoted relative to one another while still maintaining the rotationally locked link interface 160.

Figure 7C:
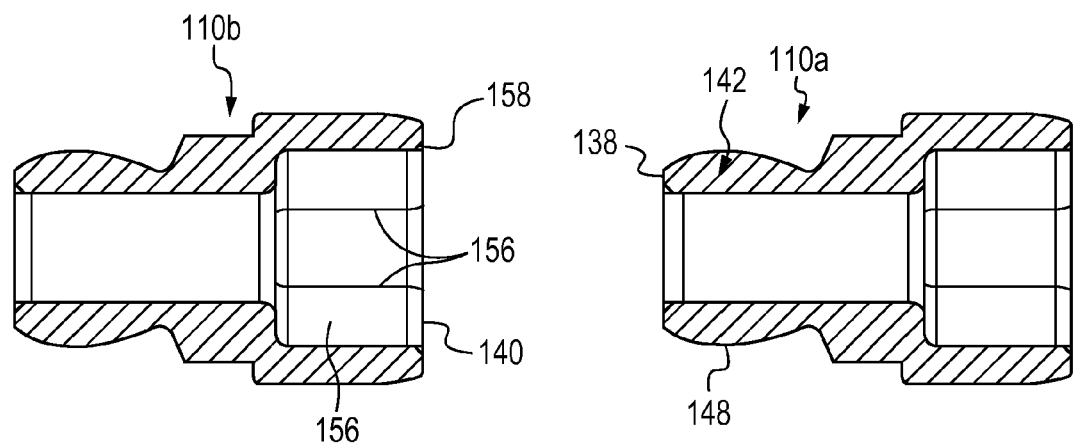

For reasons made clear below, in some embodiments of the surgical instruments 50 (FIG. 1) of the present disclosure, the adjacent links 110a, 110b are periodically separated from one another (e.g., the first link 110a is physically distanced from the second link 110b) and then re-connected. The links 110 optionally incorporate one or more features that promote self-aligning of the ball head 142 of the first link 110a with the receptacle 152 of the second link 110b during re-assembly of the links 110a, 110b to one another. For example, and with reference to FIG. 7C, the ball head 142 tapers in outer diameter (or other outer dimension) toward the first end 138, whereas a slightly enlarged guide surface 158 is formed at the second end 140 having a tapered shape leading to the receptacle 152. With this but one acceptable construction, as the ball head 142 of the first link 110a is directed toward the receptacle 152 of the second link 110b, the guide surface 158 guides the first end 138 of the ball head 142 into the receptacle 152 while allowing the ball head 142 to rotate relative to the receptacle 152. Thus, if the ball head corners 148 of the first link 110a are not exactly aligned with the receptacle corners 156 of the second link 110b, the first link 110a will rotate slightly relative to the second link 110b (and vice versa) until the corners 148, 156 are aligned.

Returning to FIGS. 6A-6E, the intermediate portion 132 is formed between the male and female end portions 130, 134, and forms a shoulder or flange 164 proximate the female end portion 134. The shoulder 164 provides a radially-projecting surface configured for seated engagement with a corresponding component feature of the articulation mechanism 64 (FIG. 3A) as described below.

The central bore 136 extends the entire length of the link 110, and has a minimum diameter along the male end portion 130 and the intermediate portion 132 that is sized to slidably receive at least the rod distal portion 92 (FIG. 4A). To accommodate deflection of the rod 90 during use, the link 110 can form chamfered or rounded edges 170, 172 at which the bore 136 has an expanding diameter in longitudinal extension. Finally, the bore 136 diameter expands at the female end portion 134 in forming the receptacle 152.

Figure 8:
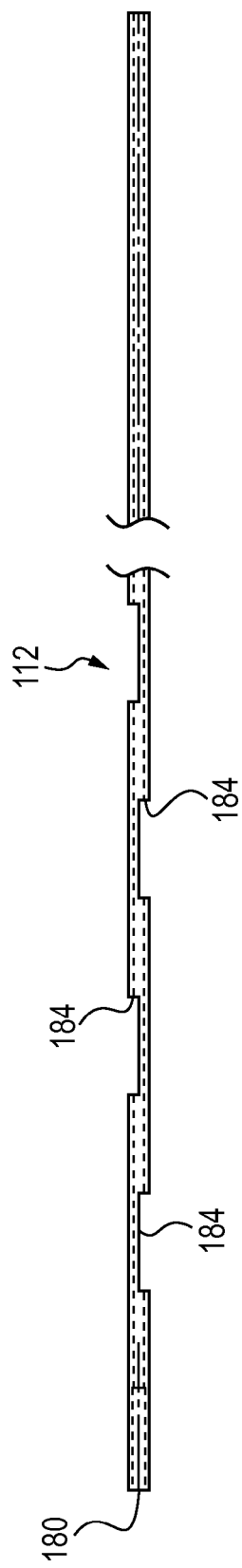
FIG. 8 is a side view of an alternative embodiment torque tube useful with the torque mechanism of FIG. 4A.

Returning to FIGS. 4A and 4B, the torque shaft 112 is sized to be received within the outer shaft 54, and has a length commensurate with that of the outer shaft 54. The torque shaft 112 terminates at a distal end 180, and can be a tubular body forming a lumen 182. The torque shaft 112 is formed of a structurally robust material (e.g., surgical grade stainless steel), and is configured to provide sufficient rigidity to maintain its structural integrity in the presence of expected torsion forces. For example, the torque shaft 112 can be constructed to maintain its structural integrity in the presence of a torsion force on the order of 0.41 in-lbf. Further, material(s) and construction selected for the torque shaft 112 are optionally able to maintain their structural integrity when subjected to repeated sterilization. In this regard, the torque shaft 112 can incorporate one or more additional features that facilitate cleaning with embodiments in which the torque shaft 112 is tubular. For example, as shown in FIG. 8, the torque shaft 112 can have several longitudinally-spaced side slots 184 through which a cleaning/sterilization fluid can be introduced for cleaning an interior of the shaft 112. Alternatively, the torque shaft 112 can be a continuous tube.

Figure 9A:
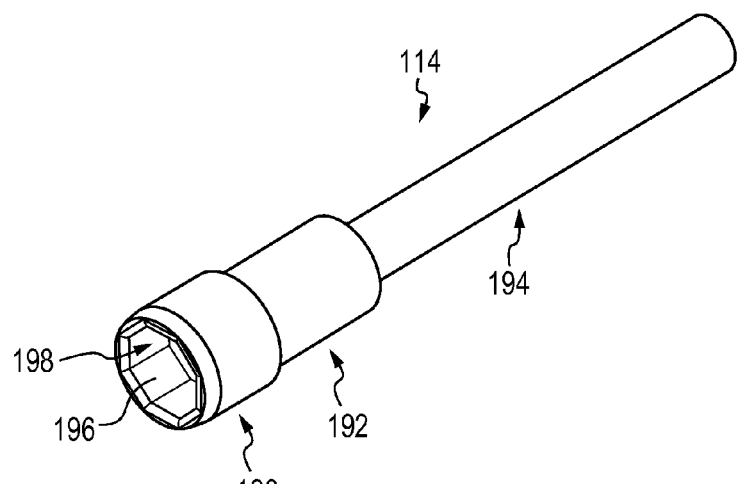
FIG. 9A is perspective view of a proximal drive body useful with the torque mechanism of FIG. 4A.
Figure 9B:
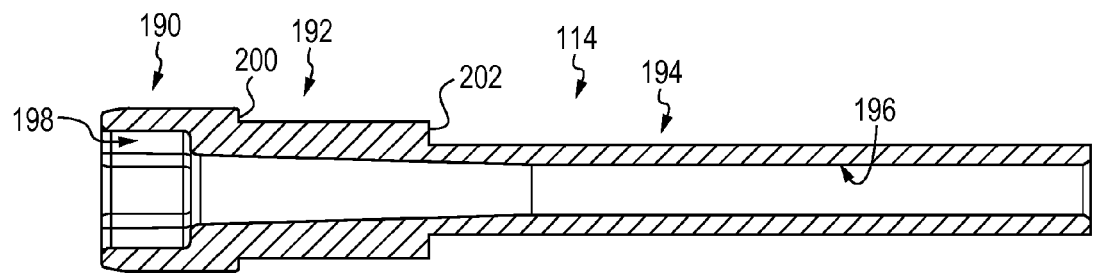
FIG. 9B is a cross-sectional view of the proximal dry body of FIG. 9A.

Returning to FIGS. 4A and 4B, and with additional reference to FIGS. 9A and 9B, the proximal drive body 114 defines a leading segment 190, an intermediate segment 192, a trailing segment 194 and a central passage 196. The proximal drive body 114 can be a homogeneous structure formed of a hardened, surgically-safe material (e.g., surgical grade stainless steel) that optionally is able to maintain its structural integrity when subjected to repeated sterilization.

The leading segment 190 is configured to connect with the proximal-most link 110p in a manner akin to the link interface 160 (FIG. 7A) described above. Thus, the leading segment 190 can be identical to the female end portion 134 provided with each of the links 110, forming a receptacle 198 that can be identical to the receptacle 152 described above (e.g., octagonal shape). The receptacle 198 is configured to receive the ball head 142 of one of the links 110 in a pivotable yet rotationally locked relationship. Alternatively, the leading segment 190 can form a ball head akin to the ball head 142 of the links 110 (and thus configured to be received within the receptacle 152 of the links 110).

The intermediate segment 192 has a reduced outer diameter as compared to the leading segment 190 and an increased outer diameter as compared to the trailing segment 194 to form first and second shoulders 200, 202. In some embodiments, the intermediate segment 192 is configured for seated assembly to a corresponding component of the articulation mechanism 64. The trailing segment 194 extends from the intermediate segment 192, and can have a relatively uniform outer diameter as shown. In this regard, an outer diameter of the trailing segment 194 corresponds with an inner diameter of the torque tube 112 for press-fitted coupling between the components 112, 114.

The central passage 196 is sized to slidably receive the rod 90 (FIG. 4A), and thus defines a minimum diameter that is greater than an outer diameter of the rod 90. To accommodate deflection of the rod 90 during use, the central passage 196 can have or define an increasing diameter from the trailing segment 194 to the leading segment 190.

With reference to FIGS. 4A, 4B, 10A and 10B, the distal drive body 116 defines a leading region 210, an intermediate region 212, a trailing region 214 and a central passageway 216. The distal drive body 116 can be a homogeneous structure formed of a hardened, surgically-safe material (e.g., surgical grade stainless steel) that optionally is able to maintain its structural integrity when subjected to repeated sterilization.

The leading region 210 is configured for connection with the distal-most link 110d in a manner akin to the link interface 160 (FIG. 7A) described above. Thus, the leading region 210 can be identical to the male end portion 130 provided with each of the links 110, forming a polygonal ball head 218 that can be identical to the polygonal ball head 142 described above (e.g., octagonal ball shape). The ball head 218 is configured to be received within the receptacle 152 of one of the links 110 in a pivotable yet rotationally locked relationship. Alternatively, the leading region 210 can form a receptacle akin to the receptacle 152 of the links 110 (and thus configured to receive the ball head 142 of the links 110).

The intermediate region 212 forms a ring 220 having an outer diameter greater than an outer diameter of the leading and trailing regions 210, 214. As described below, the ring 220 is configured for seated assembly to a corresponding component of the articulation mechanism 64. Finally, the trailing region 214 extends from the intermediate region 212 and can have the relatively uniform outer diameter as shown. To facilitate mounting with the coupling assembly 118, an optional bore 222 is formed along the trailing region 214, extending in a direction generally perpendicular to that of the passageway 216. For reasons made clear below, the bore 222 is open to the passageway 216, and extends through an entire thickness of the drive body 116.

The passageway 216 is sized to slidably receive the rod 90, and thus has a minimum diameter at least slightly larger than an outer diameter of the rod distal portion 92. To accommodate deflection of the rod 90 during use, the passageway 216 can taper from an enlarged diameter along the leading region 210, and a leading end 224 can be rounded or chamfered.

With specific reference to FIGS. 4A and 4B, the coupling assembly 118 can assume a wide variety of forms appropriate for connecting the distal drive body 116 to the end effector 52 in a rotationally fixed manner. In one embodiment appropriate for use with moveable-type end effector constructions, the coupling assembly 118 includes a clevis 230 and a king pin 232. In general terms, the king pin 232 connects the distal drive body 116 with the clevis 230, and the clevis 230, in turn, is coupled to the end effector 52. As with other components of the torque mechanism 62, the clevis 230 and the king pin 232 are formed from a hardened, surgically-safe material (e.g., surgical grade stainless steel) that optionally is able to maintain its structural integrity when subjected to repeated sterilization.

Figure 11A:
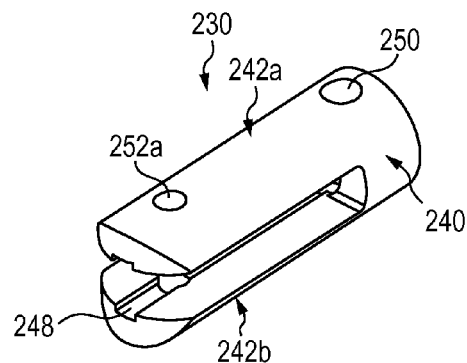
FIG. 11A is a perspective view of a clevis useful with a coupling assembly of the torque mechanism of FIG. 4A.
Figure 11B:
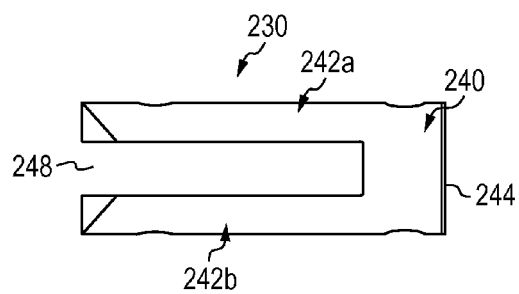
FIG. 11B is a side view of the clevis of FIG. 11A.
Figure 11C:
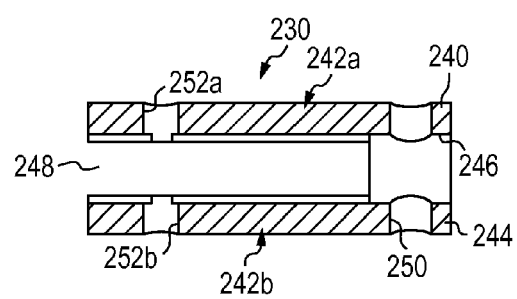
FIG. 11C is a cross-sectional view of the clevis of 11A.

The clevis 230 is shown in greater detail in FIGS. 11A-11C, and includes or defines a base 240 and opposing legs 242a, 242b. The base 240 terminates at a bearing surface 244 opposite the legs 242a, 242b, and defines a longitudinal pathway 246 that is open at the bearing surface 244 and to a gap 248 formed between the legs 242a, 242b. The pathway 244 is sized to receive the rod distal portion 92 (FIG. 4A). Further, a radially extending through-hole 250 is defined in the base 240, extending generally transversely to the pathway 244. The through-hole 250 is open to the pathway 244, and extends through an entire thickness of the base 240. As described below, the through-hole 250 is configured to receive the king pin 232 (FIG. 4A).

The legs 242a, 242b extend from the base 240 in a mirror-like fashion to form the gap 248. A size and shape of the legs 242a, 242b, and thus of the gap 248, corresponds with various features of the end effector 52 (FIG. 3A), and in particular the bodies 70, 72 (FIG. 3A) and corresponding linkages (e.g., the arms 100, 102 (FIGS. 5A and 5B)). More particularly, components of the end effector 52 are disposed within the gap 248, with the gap 248 being sized and shaped to accommodate necessary component movement during actuation of the end effector 52. With some embodiments in which the end effector 52 is akin to a grasping tool, the legs 242a, 242b are configured to facilitate pivoting connection between the end effector bodies 70, 72, such as by holes 252a, 252b formed in the legs 242a, 242b, respectively, through which a pin 254 (identified in FIG. 5B) otherwise pivotably connecting the bodies 70, 72 is captured. Due the inter-related features of the clevis 230 and the end effector 52, the clevis 230 can alternatively be viewed as being a component of the end effector 52.

Figure 10A:
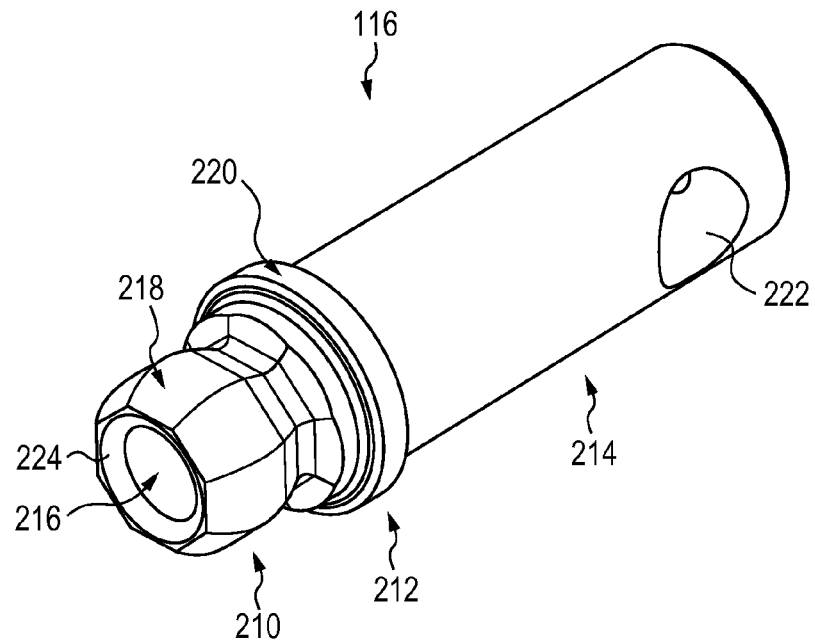
FIG. 10A is a perspective view of a distal drive body useful with the torque mechanism of FIG. 4A.
Figure 10B:
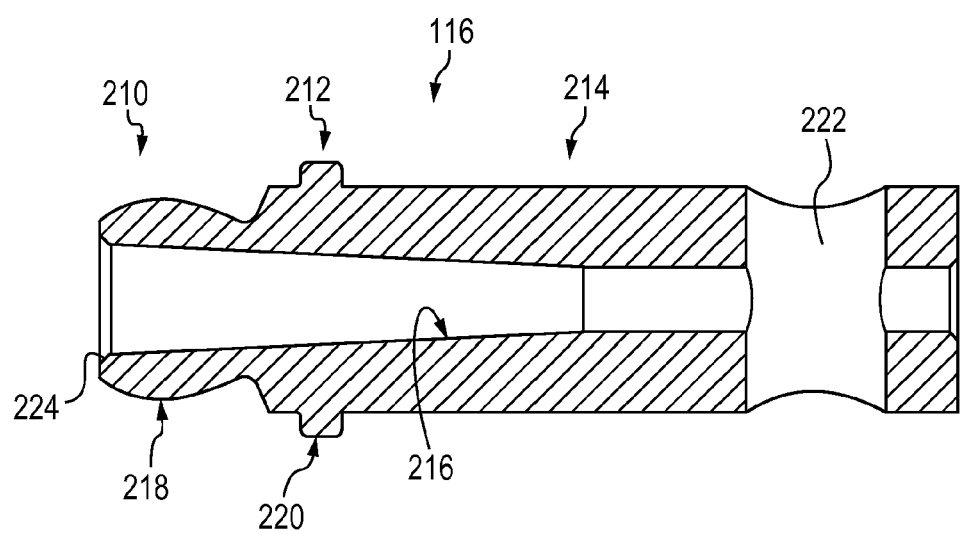
FIG. 10B is a cross-sectional view of the distal drive body of FIG. 10A.
Figure 12:
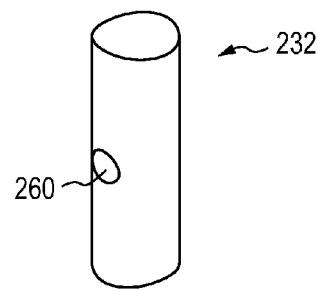
FIG. 12 is a perspective view of a king pin useful with the torque mechanism coupling assembly of FIG. 4A.

Returning to FIGS. 4A and 4B and with additional reference to FIG. 12, the king pin 232 is a solid, cylindrical body having an outer diameter commensurate with that of the clevis through-hole 250 (FIG. 11A) and of the distal drive body bore 222 (FIG. 10A). Further, a length of the king pin 232 approximates a diameter of the clevis base 240. In addition, the king pin 232 defines a radially extending rod hole 260. The rod hole 260 is sized to slidably receive the rod 90, and thus has a diameter at least slightly greater than that of the rod distal portion 92.

Figure 13:
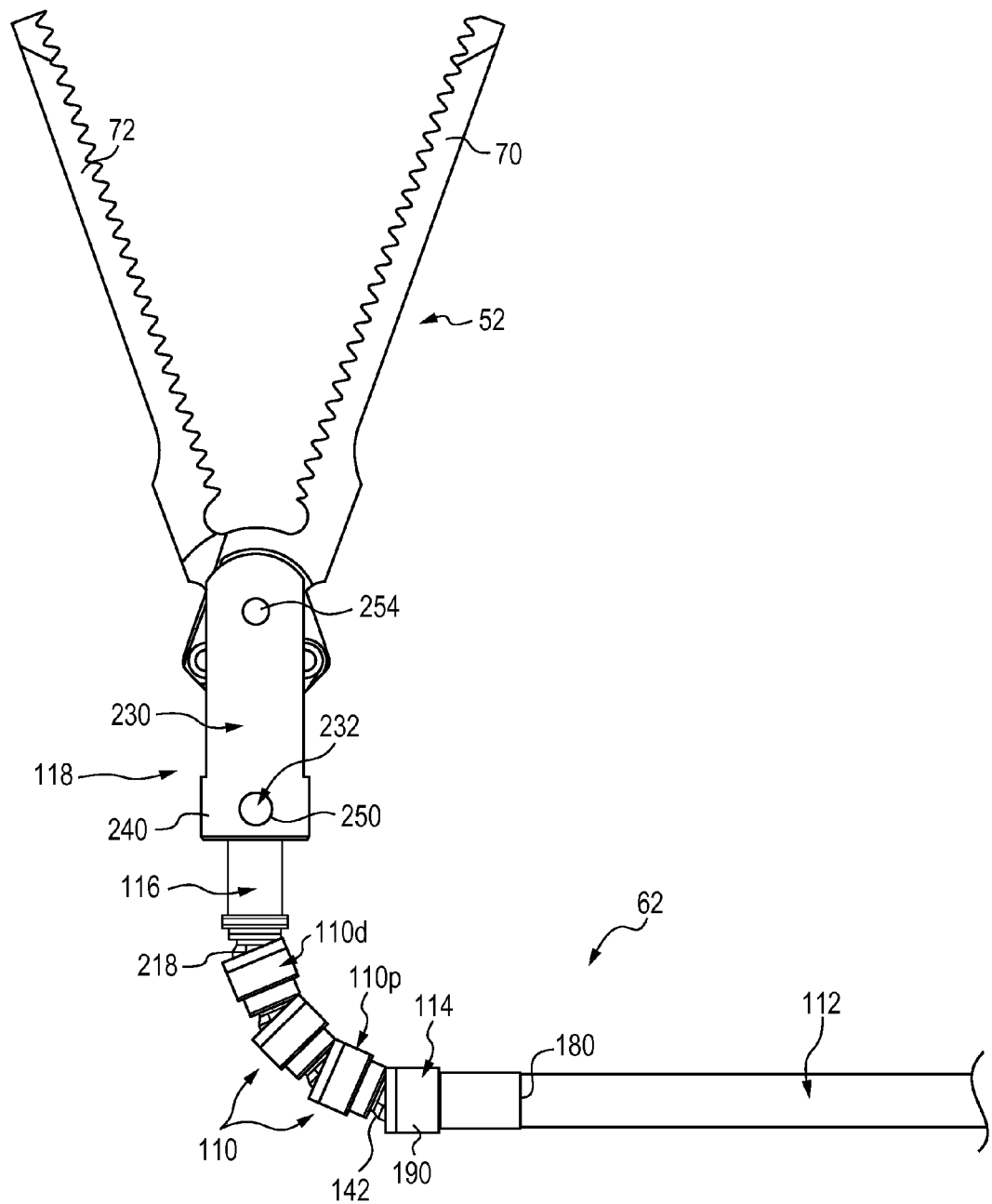
FIG. 13 is a side view of a portion of the instrument of FIG. 4A, illustrating assembly of the torque mechanism.

With cross reference between FIGS. 4A, 4B and 13, assembly of the torque mechanism 62 generally includes the proximal drive body 114 being secured to the torque shaft 112 (e.g. press fit), with the leading segment 190 projecting distal the distal end 180 of the torque shaft 112. The torque shaft 112 and the proximal drive body 114 are thus affixed to one another (i.e., rotationally and axially fixed). The distal drive body 116 is mounted to the end effector 52 via the coupling assembly 118. For example, the end effector bodies 70, 72 are pivotably secured to one another and to the clevis 230 by the pin 254 (e.g., the pin 254 can be welded or otherwise affixed to the clevis legs 242a, 242a and rotatably connected the bodies 70, 72). The trailing region 214 of the distal drive body 116 is disposed within the clevis pathway 246, and is captured relative to the clevis base 240 by the king pin 232 (e.g., the king pin 232 is lodged within the clevis through-hole 250 and the distal drive body bore 222 via a slip fit). The king pin 232 is arranged such that the king pin rod hole 260 (best shown in FIG. 12) is aligned with the distal drive body passageway 216. The rod 90 is inserted through the passageway 216 and the rod hole 260 thereby preventing lateral removal of the king pin 232 from the clevis through-hole 250 and the distal drive body bore 222. Alternatively, other configurations and/or assembly techniques can be employed to rotationally fix the distal drive body 116 with the end effector 52. For example, where the end effector 52 has a non-moving construction (e.g., electrode probe), a simple direct mounting between the end effector 52 and the distal drive body 116 can be employed. Finally, the links 110 are consecutively arranged between the proximal and distal drive bodies 114, 116. As shown, the ball head 142 of the proximal-most link 110p is received within the receptacle 198 of the proximal drive body 114, and the ball head 218 of the distal drive body 116 is received within the receptacle 152 of the distal-most link 110d. The remaining intermediate links 110 are arranged in the end-to-end fashion shown.

In the connected or chain arrangement of the links 110, a pivoting, rotationally fixed joint is established between the proximal-most link 110p and the proximal drive body 114, between adjacent ones of the links 110, and between the distal-most link 110d and the distal drive body 116. Thus, the connected links 110 can readily transition through various shapes or curvatures collectively defined by the links 110 yet still transmit a torque or rotational force from the torque shaft 112 to the end effector 52. Although the links 110 are shown as physically connected to one another in the views of FIGS. 4A, 4B and 13, it will be understood that the links 110 are discrete components and in some embodiments, are not permanently connected or coupled to one another. That is to say, the proximal-most link 110p can be physically removed from engagement with the proximal drive body 114, adjacent ones of the links 110 can be physically separated from one another, and the distal-most link 110d can be physically separated from the distal drive body 116, such as in an optional cleaning mode of the instrument 50 described below. As a point of reference, in some embodiments the links 110 are collectively brought into, and held in, engagement with one another and the drive bodies 114, 116 by features of the articulation mechanism 64 as described below.

Articulation Mechanism 64

Returning to FIGS. 4A and 4B, the articulation mechanism 64 includes the deflection section 66, a proximal joint connector 300, a distal joint connector 302, a first cable segment 304 and a second cable segment 306. In general terms, the proximal joint connector 300 connects the deflection section 66 with the outer tube 54, and the distal joint connector 302 connects the deflection section 66 with the end effector 52. The cable segments 304, 306 associate components of the deflection section 66 with one another and the joint connectors 300, 302, and are operable in a reciprocating manner to effect a change in shape or articulation along the deflection section 66.

The deflection section 66 includes or is comprised of a plurality of articulation members 310. The articulation members 310 can be identical, and FIGS. 14A-14D illustrate one of the articulation members 310 in greater detail. The articulation member 310 can be an integrally formed, homogeneous structure formed of a hardened, surgically-safe material (e.g., surgical grade stainless steel) that is optionally able to maintain its structural integrity when subjected to repeated sterilization. The articulation member 310 includes or defines a central section 312, a female section 314 and a male section 316. The female and male sections 314, 316 extend in opposing directions from the central section 312 and are generally configured such that the female section 314 of one articulation member 310 mates with the male section 316 of a second articulation member 310.

Figure 14A:
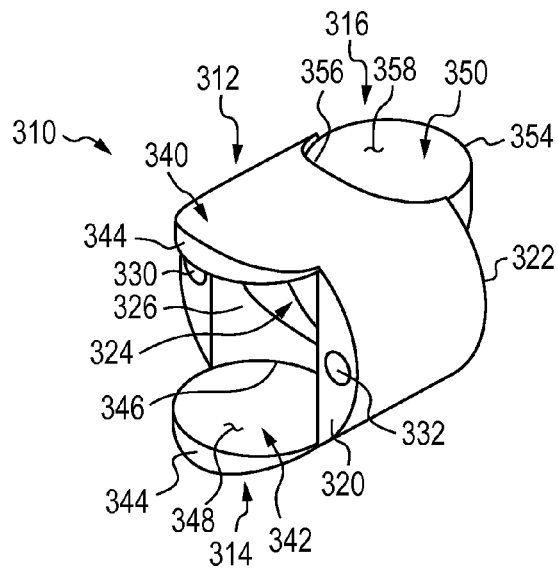
FIG. 14A is a perspective view of an articulation member useful with an articulation mechanism of the wrist assembly of FIG. 3A.
Figure 14B:
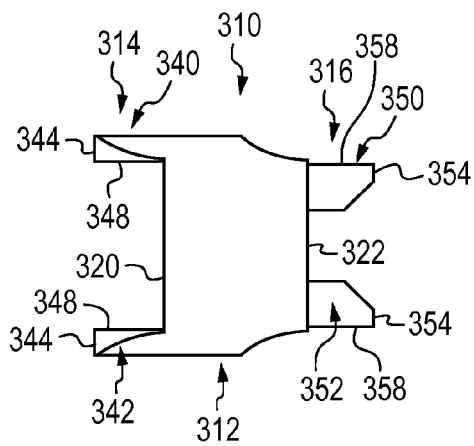
FIG. 14B is a side view of the articulation member of FIG. 14A.
Figure 14C:
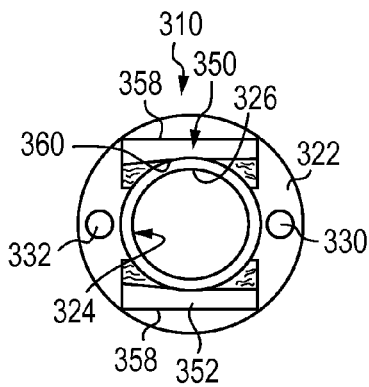
FIG. 14C is an end view of the articulation member of FIG. 14A.
Figure 14D:
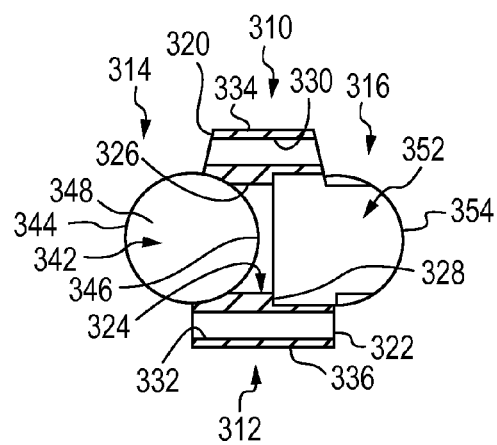
FIG. 14D is cross-sectional view of the articulation member of FIG. 14A.

The central section 312 can be generally cylindrical, and forms opposing, first and second faces 320, 322. A center passage 324 extends through the central section 312, and is open at the opposing faces 320, 322. The passage 324 is defined by an interior surface 326 of the central section 312, and is sized and shaped to receive one of the links 110 (FIG. 6A). It will be recalled that the links 110, in turn, are configured to slidably receive the rod distal portion 92 (FIG. 4A); thus, the passage 324 is also larger than a diameter of the rod distal portion 92. As best shown in FIG. 14D, the central section 312 defines a shelf 328 along a length of the interior surface 326, with the passage 324 having an increased diameter from the shelf 328 to the second face 322. The shelf 328 is configured to interface or mate with a corresponding feature of the links 110 as described below.

In addition to the center passage 324, the central section 312 forms first and second side channels 330, 332. The side channels 330, 332 extend between, and are open at, the faces 320, 322, and are located opposite one another relative to the center passage 324. In some embodiments, the side channels 330, 332 are centrally located relative to projecting features of the female section 314 and of the male section 316. Regardless, each of the side channels 330, 332 is sized to slidably receive a corresponding one of the cable segments 304, 306 (FIG. 4A).

Relative to a transverse cross-sectional plane through the articulation member 310 (i.e., FIG. 14D), the central section 312 can be viewed as defining opposing sides 334, 336. In some embodiments, the central section 312 is shaped such that the first side 334 is shorter than the second side 336. In other words, a length of the first side 334 between the opposing faces 320, 322 is less than a length of the second side 336 between the opposing faces 320, 322. As shown, the reduced length of the first side 334 can include the central section 312 tapering in length to the first side 334. Regardless, the reduced length of the first side 334 can facilitate formation of a more pronounced curvature in the deflection section 66 (FIG. 3A) as described below. Alternatively, the central section 312 can be uniform in length.

The female section 314 includes opposing, first and second fingers 340, 342 that project longitudinally outwardly from the first face 320 at opposite sides of the center passage 324. The fingers 340, 342 can be identical in size and shape, and each terminate in a rounded or circular end 344. As best reflected in FIG. 14D, the rounded end 344 can have a uniform radius of curvature approximating a semi-circle. A circular shape defined by the rounded end 344 is optionally continued into the interior surface 326 of the central section 312, resulting in a curved ridge 346 (best shown in FIG. 14A relative to the second finger 342). An inner face 348 of each of the fingers 340, 342 is thus effectively continuous from the corresponding end 344 to the corresponding ridge 346.

The male section 316 includes opposing, first and second tabs 350, 352 that project longitudinally outwardly from the second face 322 at opposite sides of the center passage 324. The tabs 350, 352 can be identical in size and shape, and each terminates in a rounded or curved tip 354 opposite the second face 322. The rounded tip 354 can have the same, uniform radius of curvature of the fingers 340, 342. Similarly, the circular shape is continued into a thickness of the central section 312, generating a curved edge 356 (best shown in FIG. 14A relative to the first tab 350). An outer surface 358 of each of the tabs 350, 352 is substantially flat, whereas an inner surface 360 can have a curvature approximating that of the center passage 324 as shown in FIG. 14C.

Figure 15A:
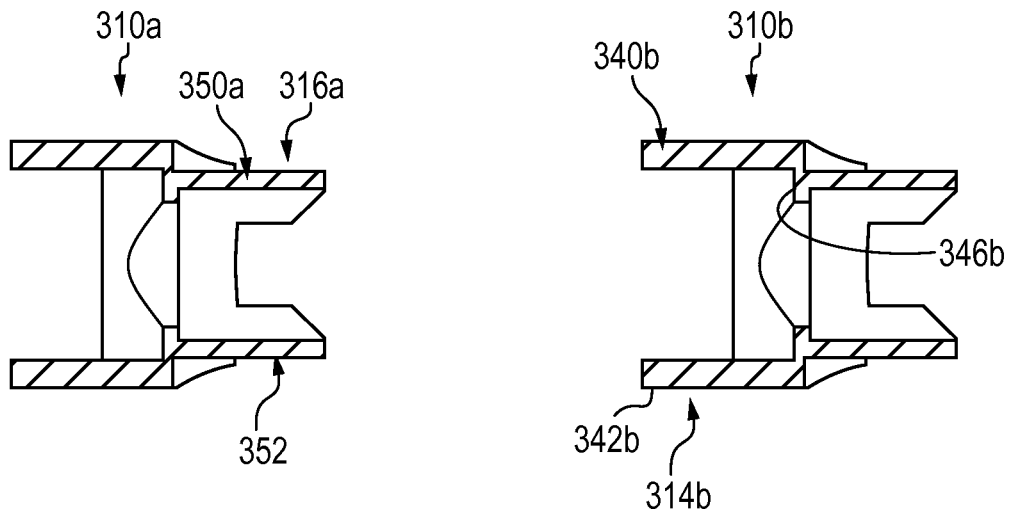
FIGS. 15A-15D are cross-sectional views illustrating connection between two of the articulation members of FIG. 14A.
Figure 15B:
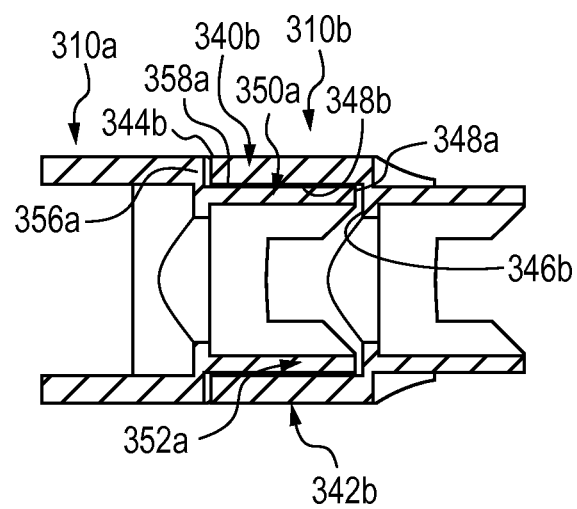
Figure 15C:
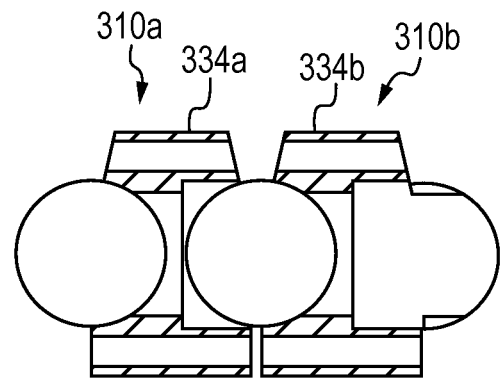
Figure 15D:
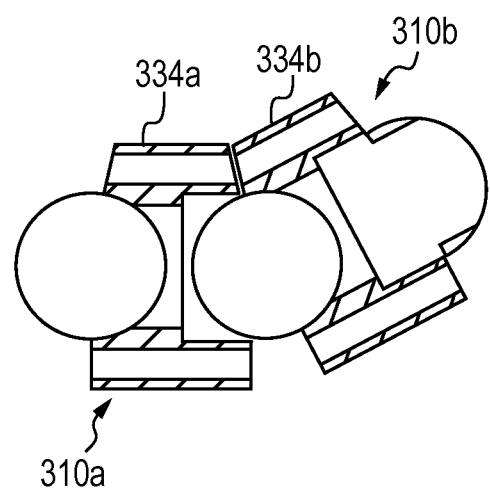

A lateral spacing between the fingers 340, 342 corresponds with a lateral spacing between the tabs 350, 352. For example, the lateral distance between the inner faces 348 of the fingers 340, 342 is the same as, or slightly larger than, the lateral distance between the outer surfaces 358 of the tabs 350, 352. This matched spacing, as well as corresponding shapes of the fingers 340, 342, the ridges 346, the tabs 350, 352, and the edges 356, facilitates a pivoting interface or connection between two adjacent ones of the articulation members 310. FIG. 15A illustrates first and second articulation members 310a, 310b poised for connection with one another (with references numbers provided below for each of the articulation members 310a, 310b including the corresponding designation of "a" or "b"). The male section 316a of the first articulation member 310a faces the female section 314b of the second articulation member 310b. Upon final connection as in FIG. 15B, the first finger 340b rides over the first tab 350a, including the finger inner face 348b abutting the tab outer surface 358a. The rounded end 344b of the first finger 340b nests against the rounded edge 356a associated with the first tab 350a. Further, the rounded tip 354a of the first tab 350a nests against the ridge 346 associated with the first finger 340b. A similar interface is provided between the second finger 342b and the second tab 352a. With this connection, the first and second articulation members 310a, 310b can pivot relative to one another, rotating about a hypothetical centerline passing through the aligned, circular shapes of the fingers 340b, 342b and the tabs 350a, 352a. As a point of reference, FIG. 15C illustrates the assembly of FIG. 15B but from a plane perpendicular to that of FIG. 15B and reflects that the articulation members 310a, 310b are arranged to align the shorter first sides 334a, 334b with one another. A longitudinal spacing between the first sides 334a, 334b provides sufficient clearance for pivoting of the articulation members 310a, 310b relative to one another in a direction of the first sides 334a, 334b. For example, FIG. 15D shows the second articulation member 310b pivoted relative to the first articulation member 310a, with the first sides 334a, 334b allowing for a relatively large range of articulation between the two members 310a, 310b.

Returning to FIGS. 4A and 4B and with additional reference to FIGS. 16A-16E, the proximal joint connector 300 can be a homogeneous body formed of a hardened, surgically-safe material (e.g., surgical grade stainless steel) that is optionally able to maintain its structural integrity when subjected to repeated sterilization. The proximal joint connector 300 can be akin to the articulation members 310, and includes or defines a hub 370, a leading portion 372 and a trailing portion 374.

Figure 16A:
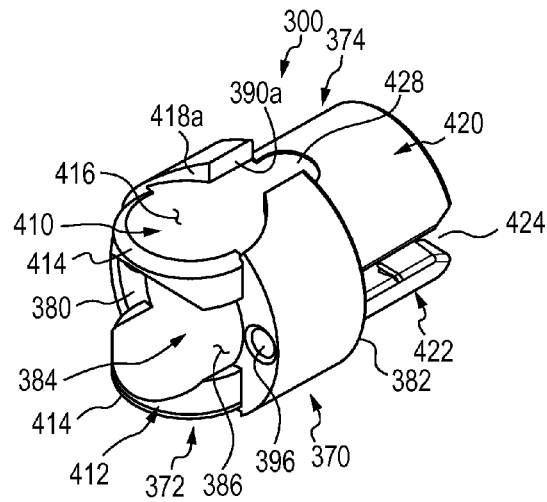
FIG. 16A is perspective view of a proximal joint connector useful with the articulation mechanism of FIG. 3A.
Figure 16B:
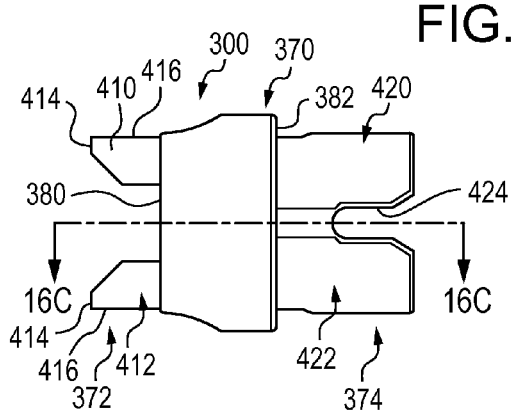
FIG. 16B is side view of the proximal joint connector of FIG. 16A.
Figure 16C:
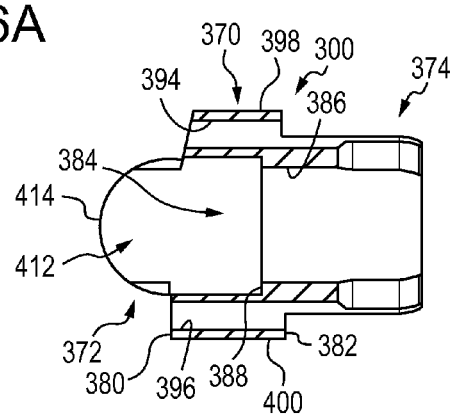
FIG. 16C is a cross-sectional view of the proximal joint connector of FIG. 16B, taken along the line 16C-16C.
Figure 16D:
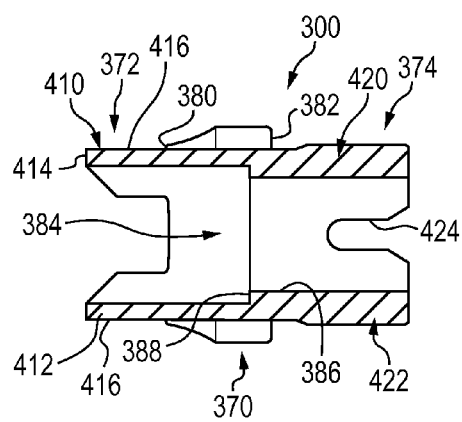
FIG. 16D is another cross-sectional view of the proximal joint connector of FIG. 16A taken in a plane 90 degrees from that of FIG. 16C.
Figure 16E:
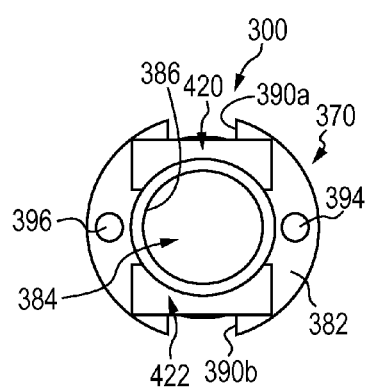
FIG. 16E is an end view of the proximal joint connector of FIG. 16A.

The hub 370 can be generally cylindrical, and forms opposing first and second faces 380, 382. A central passageway 384 extends longitudinally through the hub 370 and is open at the opposing faces 380, 382. The passageway 384 is defined by an interior surface 386. A step 388 is formed along the interior surface 386, with the passageway 384 having an increased diameter from the step 388 to the first face 380. The step 388 is configured to receive a feature provided with the proximal drive body 114 as described below. The hub 370 further forms optional slots 390a, 390b at an exterior thereof for receiving respective ones of the outer shaft tines 82a, 82b (FIG. 2A). Opposing side channels 394, 396 are defined at opposite sides of the central passageway 384, and are sized to slidably receive a respective one of the cable segments 304, 306. Finally, and as best shown in FIG. 16C, the hub 370 can be configured to define (relative to the cross-sectional plane illustrated) a first side 398 that is shorter than an opposite, second side 400.

The leading portion 372 can be identical to the articulation member male section 316 (FIG. 14A) and thus includes opposing tabs 410, 412 projecting from the first face 380 and each terminating in rounded or curved tip 414 defining the semi-circular shape mentioned above. An outer surface 416 of each of the tabs 410, 412 is flattened, with a curvature defined by the rounded tip 414 continuing into a thickness of the hub 370 so as to form curved edge segments 418a, 418b (shown with respect to the first tab 410 in FIG. 16A). The edge segments 418a, 418b are separated by the corresponding slot 390a or 390b, but collectively define a radius of curvature corresponding with that of the rounded tip 404.

The trailing portion 374 includes opposing arms 420, 422 projecting from the second face 382. The arms 420, 422 are circumferentially separated from one another by a gap 424 sized to provide clearance about a respective one of the cable segments 304, 306. In this regard, the arms 420, 422 are arcuate in shape (best shown in FIG. 16A) and collectively define an outer diameter approximating an inner diameter of the outer shaft lumen 89 (FIG. 2B) and the distal end 80 (FIG. 2B) thereof. To facilitate a rotationally locked assembly with the outer shaft 54 in which the outer shaft tines 82*a*, 82*b* (FIG. 2A) are received within a corresponding hub slot 390*a*, 390*b*, an exterior 426 of each of the arms 420, 422 optionally forms a flattened surface 428 (identified in FIG. 16A) adjacent the hub 370. Where provided, the flattened surface 428 can facilitate sliding insertion of the outer shaft tines 82*a*, 82*b* into the corresponding slot 390*a*, 390*b*.

The distal joint connector 302 is shown in greater detail in FIGS. 17A-17D, and is provided as a homogeneous body formed of a hardened, surgically-safe material (e.g., surgically grade stainless steel) that is optionally able to maintain its structural integrity when subjected to repeated sterilization. The distal joint connector 302 defines or forms a head 430 and a rearward region 432. The head 430 can have the generally cylindrical shape shown. A central passage 434 and opposing side channels 436, 438 extend through a length of the head 430, and are open at opposing first and second faces 440, 442 thereof. The central passage 434 is configured to mate with surface features of the distal drive body 116 (FIG. 10A). For example, the central passage 434 is defined by an interior surface 444 that forms a trough 446. A diameter of the passage 434 is increased at the trough 446 in a direction of the first face 440. An optional circumferential slot 448 is formed adjacent the second face 442 and is open to the side channels 436, 438 as well as to an exterior 450 of the head 430. As described below, where provided, the slot 448 is sized and shaped for guiding a cable between the side channels 436, 438. Finally, in some embodiments, the head 430 is shaped to define a first side 452 having a length less than a length of an opposing second side 454, as best reflected in the cross-sectional view of FIG. 17C.

The rearward region 432 can be akin to the articulation member female section 314 (FIG. 14A) and includes opposing, first and second fingers 460, 462. The fingers 460, 462 project longitudinally outwardly from the first face 440 and each terminate in a rounded end 464. The fingers 460, 462 are arranged at opposite sides of the central passage 434, and each define an interior face 466 configured to receive a corresponding one of the articulation member tabs 350, 352 (FIG. 14A). As with the articulation members 310, the circular shape of the rounded end 464 continues along the interior surface 444 of the head 430, forming a curved ridge 468.

With specific reference to FIGS. 4A and 4B, the cable segments 304, 306 are sized to be slidably received within one of the side channels 330, 332, 394, 396, 436, 438 of the articulation members 310, the proximal joint connector 300 and the distal joint connector 302, respectively. In some embodiments, the cable segments 304, 306 are defined by a single cable that is partially wound about the distal joint connector 302 as described below. In other embodiments, the cable segments 304, 306 can be separate, discrete cables. Regardless, the segments 304, 306 are configured to apply necessary tension onto the deflection section 66, and can be metal wires, braids, flat bands, etc.

Assembly of the articulation mechanism 64 between the outer shaft 54 and the end effector 52 is, in some embodiments, directly related to the torque mechanism 62 and corresponding assembly of the torque mechanism 62 between the outer shaft 54 and the end effector 52. This optional relationship is described in detail below. In more general terms and as reflected in FIGS. 3A and 3B, the proximal joint connector 300 is connected to the outer shaft 54, the distal joint connector 302 is coupled to the end effector 52, and the plurality of articulation members 310 are consecutively arranged between the joint connectors 300, 302 in an end-to-end fashion. The proximal-most articulation member 310*p* is arranged relative to the proximal joint connector 300 such that the fingers 340, 342 (one of which is visible in FIGS. 3A and 3B) of the proximal-most articulation member 310*p* are received over (or can be received over) a corresponding one of the tabs 410, 412 (FIG. 16A) of the proximal joint connector 300 in a manner akin to the arrangement described above with respect to FIGS. 15A and 15B. As with the arrangement between adjacent ones of the articulation members 310, the fingers 340, 342 slidingly abut the corresponding curved edge segments 418*a*, 418*b* (one of which is visible in FIGS. 3A and 3B) such that the proximal-most articulation member 310*p* readily pivots relative to the proximal joint connector 300 upon final assembly. Similarly, the distal-most articulation member 310*d* is arranged relative to the distal joint connector 302 such that the fingers 460, 462 (one of which is visible in FIGS. 3A and 3B) of the distal joint connector 302 are received over a corresponding one of the tabs 350, 352 (FIG. 14A) of the distal-most articulation member 310*d*. The rounded end 464 of each of the fingers 460, 462 slidingly abuts the corresponding curved edge 356 such that the distal-most articulation member 310*d* readily pivots relative to the distal joint connector 300 upon final assembly. Intermediate ones of the articulation members 310 are consecutively arranged between the proximal-most and distal-most articulation members 310*p*, 310*d* as described above. As best shown in FIGS. 4A and 4B, the first cable segment 304 is disposed within the first side channel 330, 394, 436 of the articulation members 310, the proximal joint connector 300 and the distal joint connector 302, respectively; and the second cable segment 306 is disposed within the second side channel 332, 396, 438 of the articulation members 310, the proximal joint connector 300 and the distal joint connector 302, respectively. In this regard, where the cable segments 304, 306 are formed by a single cable, the cable is threaded through the slot 448 of the distal joint connector 302. Regardless, and as shown in FIGS. 3A-4B, the components 300, 302, 310 are arranged such that the shorter, first sides 334, 398, 452 are aligned with one another, as are the longer, second sides 336, 400, 454.

Wrist Assembly General Construction and Operation

In general terms, construction of the wrist assembly 56 can include connecting the torque mechanism 62 and the articulation mechanism 64 with the outer shaft 54. The rod 90 is inserted through the torque shaft 112 to locate the distal end 94 distal the deflection section 66. The distal drive body 116 is secured to the clevis 320 via the king pin 232. The rod distal end 94 is inserted through the distal drive body 114 and the king pin 232, and the rod distal end 94 is secured to the end effector 52.

Figure 18A:
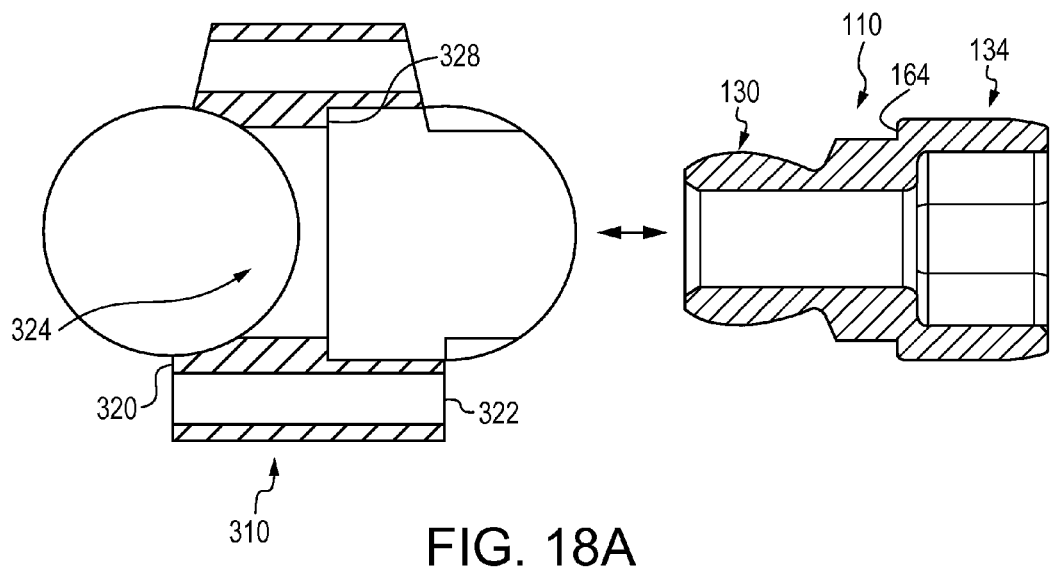
FIGS. 18A and 18B illustrate connection between one of the links of FIG. 6A and one of articulation member of FIG. 14A.
Figure 18B:
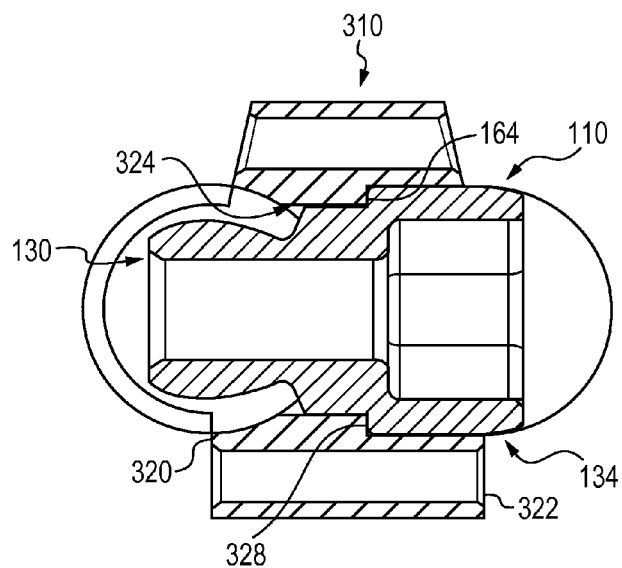

Assembly of the torque mechanism 62 and the articulation mechanism 64 are inter-related in some embodiments, with the resultant construction permitting operation of each mechanism 62, 64 independent of the other (and of the end effector operation mechanism 60). One aspect of the inter-related relationship is reflected in FIGS. 18A and 18B that otherwise illustrate assembly of one of the links 110 with one of the articulation members 310. The link 110 is received within the passage 324 of the articulation member 310, with the link shoulder 164 seated against the articulation member shelf 328. The male end portion 130 of the link 110 projects beyond, and is accessible relative to, the first face 320 of the articulation member 310, whereas the female end portion 134 projects beyond, and is accessible relative to, the second face 322. The seated relationship between the link 110 and the articulation member 310 is such that the link 110 freely rotates relative to the articulation member 310. However, the components 110, 310 are longitudinally coupled such that a longitudinal force applied to the articulation member 310 in one direction (e.g., rightward in the orientation of FIG. 18B) is transferred directly to the link 110, dictating that the link 110 will move with any movement of the articulation member 310 in that one direction. Conversely, the link 110 can be removed from the articulation member 310 in an opposite longitudinal direction (e.g., relative to the orientation of FIG. 18B, the link 110 can be dislodged from the articulation member 310 when the link 110 is pulled rightward and the articulation member 310 is held stationary).

Figure 19:
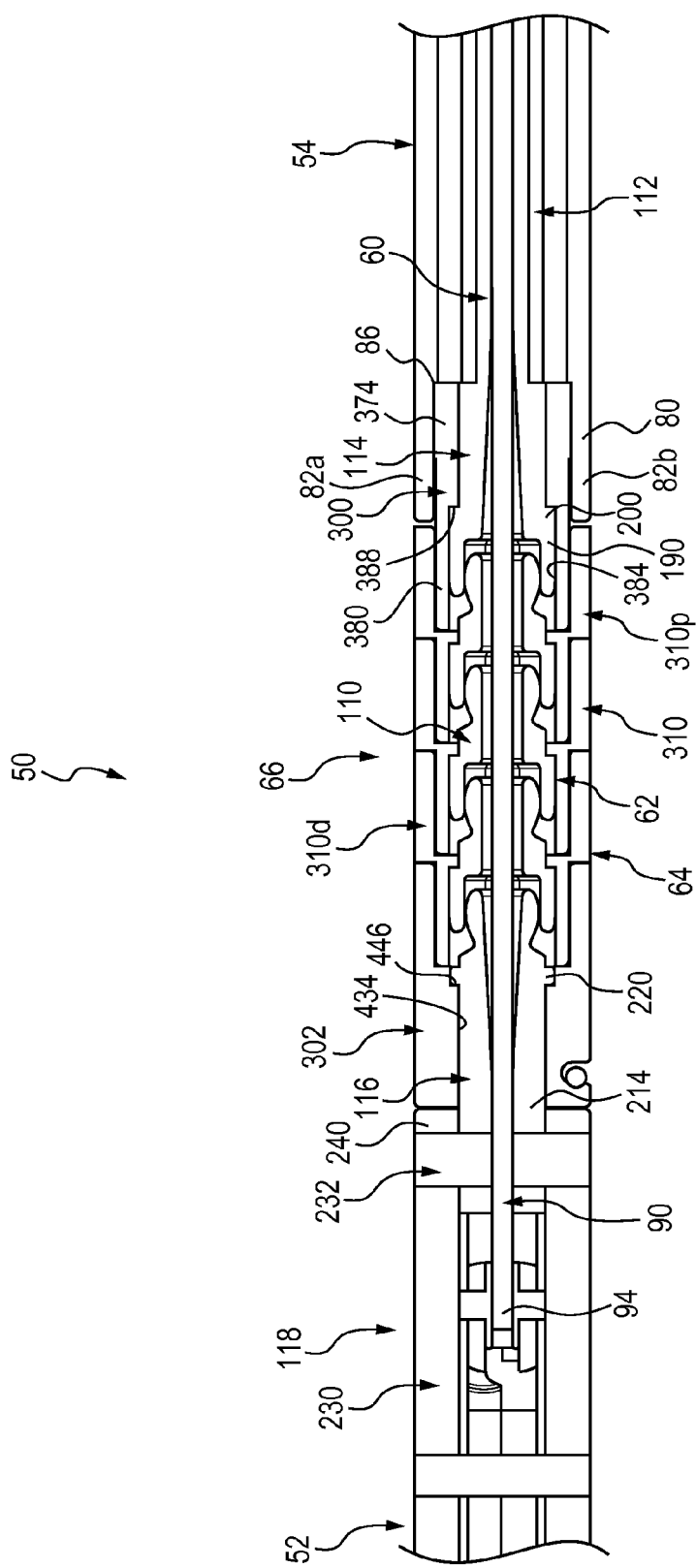
FIG. 19 is an enlarged, cross-sectional view of the wrist assembly of FIG. 3B taken in a plane 90 degrees to that of FIG. 4B and illustrating various component relationships upon final assembly.

A similar relationship is established between the distal drive body 116 and the distal joint connector 302 as shown in FIG. 19 and effectuates, in some embodiments, coupling of the distal joint connector 302 with the end effector 52. As previously described, in some embodiments, coupling of the distal drive body 116 with the end effector 52 is accomplished with the clevis 230 of the coupling assembly 118. Prior to assembly of the distal drive body trailing region 214 within the clevis base 240, the distal joint connector 302 is assembled to the distal drive body 116. For example, the distal drive body 116 is received within the distal joint connector central passage 434, with the ring 220 of the distal drive body 116 seating against the trough 446 of the distal joint connector 302. Once again, the seated arrangement is such that the distal drive body 116 can freely rotate relative to the distal joint connector 302. However, a longitudinal force imparted upon the distal joint connector 302 in one direction is transferred to the distal drive body 116 such that the distal drive body 116 will move in the direction of the so-applied force (or, more particularly, can serve to resist movement of the distal joint connector 302 in response to the so-applied force). Upon subsequent assembly of the distal drive body 116 to the coupling assembly 118, then, the distal joint connector 302 is coupled to the end effector 52.

A similar, seated assembly is provided, in some embodiments, between the proximal drive body 114 and the proximal joint connector 300. For example, the proximal drive body 114 is received within the proximal joint connector passageway 384, with the leading segment 190 of the proximal drive body 114 being accessible relative to the first face 380 of the proximal joint connector 300. The shoulder 200 of the proximal drive body 114 is seated against the step 388 of the proximal joint connector 300, with the seated arrangement such that the proximal drive body 114 can freely rotate relative to the proximal joint connector 300.

As described above, the proximal drive body 114 is coupled to the torque shaft 112. The proximal joint connector 300 is assembled over the proximal drive body 114, and then coupled to the outer shaft 54. For example, the trailing portion 374 of the proximal joint connector 300 is seated within the distal end 80 of the outer shaft 54, with the tines 82a, 82b nesting within the slots 390a, 390b(hidden in FIG. 19, but shown in FIG. 16E). An end of the proximal joint connector 300 is received against the stop surface 86 of the outer shaft 54. Notably, however, the proximal joint connector 300 and the outer shaft 54 are only rotationally engaged. The proximal joint connector 300 can be removed longitudinally (in the distal direction) from the outer shaft distal end 80.

Figure 17A:
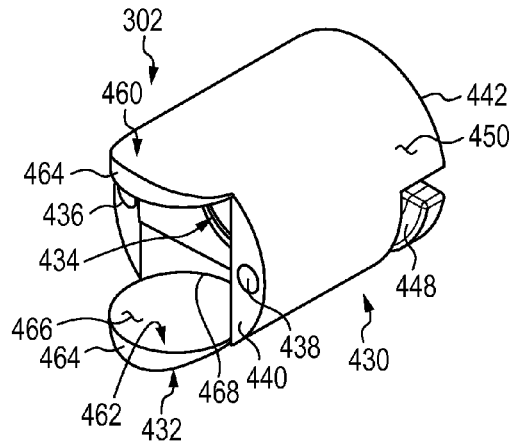
FIG. 17A is a perspective view of a distal joint connector useful with the articulation mechanism of FIG. 3A.
Figure 17B:
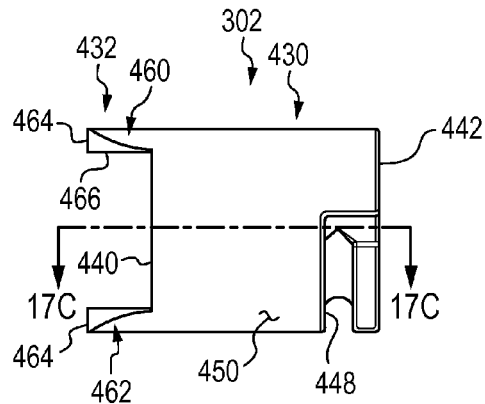
FIG. 17B is a side view of the distal joint connector of FIG. 17A.
Figure 17C:
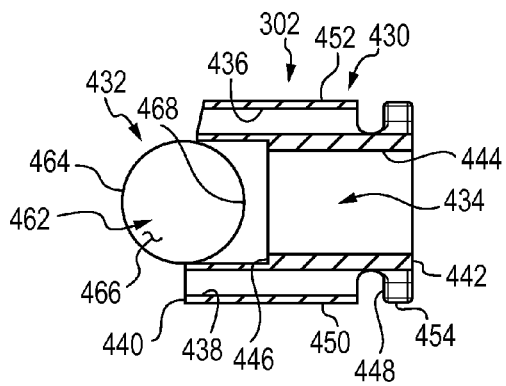
FIG. 17C is a cross-sectional view of the distal joint connector of FIG. 16B, taken along the lines 17C-17C.
Figure 17D:
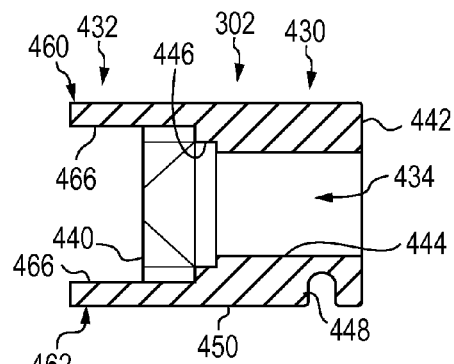
FIG. 17D is another cross-sectional view of the distal joint connector of FIG. 17A taken in a plane 90 degrees to that of FIG. 17C.

Commensurate with the above explanations and with additional reference to FIGS. 4A and 4B, following coupling of the rod distal end 94 to the end effector 52 (it being recalled that the distal drive body 116 and the distal joint connector 302 were previously mounted to the end effector 52), the cable segments 304, 306 are extended proximally from the side channels 436, 438, respectively, of the distal joint connector 302. Where the cable segments 304, 306 are formed from a single, continuous cable, the cable can be wrapped through and slidably retained within the circumferential slot 448 (FIG. 17B). Regardless, articulation member 310/link 110 pairs are consecutively loaded to the cable segments 304, 306 via the articulation member side channels 330, 332. The proximal joint connector 300 is mounted over the proximal drive body 114, and the cable segments 304, 306 threaded through the proximal joint connector side channels 394, 396. The proximal drive body 114 is attached to the torque shaft 112, and the proximal joint connector 300 is seated in the outer shaft 54 (with the cable segments 304, 306 extending in the proximal direction between the torque shaft 112 and the outer shaft 54).

In light of the above, in some embodiments, surgical instruments of the present disclosure include an equal number of links 110 and articulation members 310. In other words, each one of the links 110 is assembled to a corresponding one of the articulation member 310. The cable segments 304, 306 effectively complete the operational connection of not only the remaining articulation mechanism 64 components, but also operational connection of the torque mechanism 62 components. In particular, the cable segments 304, 306 interconnect the articulation members 310 with each other and with the joint connectors 300, 302. Because the articulation members 310 are longitudinally coupled with corresponding ones of the links 110 (and the joint connectors 300, 302 with the corresponding drive bodies 114, 116), the cable segments 304, 306 thus effectively inter-connect the links 110 with the drive bodies 114, 116. As result, when the cable segments 304, 306 are placed into tension, the distal joint connector 302 is tensioned or pulled toward the proximal joint connector 300; this tensioning force, in turn, is transferred onto to the distal-most articulation member 310d via the distal joint connector 302 being drawn into physical contact with the distal-most articulation member 310d. The remaining articulation members 310 are similarly acted upon, drawing the articulation members 310 into physical contact with one another, and the proximal-most articulation member 310p into physical contact with the proximal joint connector 300. The distal drive body 116 and the links 110 are similarly drawn toward the proximal drive body 114, with the links 110 and the proximal drive body 114 sliding over the rod 90. Thus, with tensioning of the cable segments 304, 306, the links 110 are operatively connected with one another and with the drive bodies 114, 116.

Articulation or bending of the deflection section 66 is achieved by pulling on the first (e.g., ventral) cable segment 304 (while possibly lessening tension in the second cable segment 306), whereas straightening of the deflection section 66 is achieved by pulling on the second (e.g., dorsal) cable segment 306 (while possibly lessening tension in the first cable segment 304). The so-applied tension or force is transferred to the distal joint connector 302, causing the articulation members 310 to collectively move or pivot relative to one another along the "side" at which the tension is applied.

The torque mechanism 62 can operate independent of the articulation mechanism 64, including the links 110 and drive bodies 114, 116 freely rotating relative to the corresponding articulation members 310 and joint connectors 300, 302. While the articulation mechanism 64 also operates independent of the torque mechanism 62 (i.e., the articulation mechanism 64 is operable regardless of an operational state of the torque mechanism 62), the functional effects of the articulation mechanism operation are transferred to the torque mechanism 62 in certain respects. More particularly, any deflection or bending of the deflection section 66 (as effectuated by pivoting movement of individual ones of the articulation members 310 relative to one another) is transferred to the links 110 (with corresponding, individual ones of the links 110 pivoting relative to one another in a similar fashion).

In some embodiments, the wrist assembly 56 is configured to permit rotation of the outer shaft 54 relative to the torque shaft 112 and the rod 90. Rotation of the outer shaft 54 is transferred to the articulation mechanism 64 and thus to the end effector 52, with the articulation mechanism 64 rotating relative to the torque mechanism 62 and the end effector operation mechanism 60. The articulation mechanism 64 retains the shape or curvature defined along the deflection section 66 while spatially rotating with rotation of the outer shaft 54.

Handle Assembly 58

As previously mentioned, each of the mechanisms 60-64 can include one or more additional proximal components formed at and/or carried by the handle assembly 58 (FIG. 1). In general terms, the handle assembly 58 can assume a wide variety of forms. In some embodiments, the handle assembly 58 is configured for direct physical handling by one or both of the surgeon's hands. In other embodiments, the handle assembly 58 is configured for remote interface by the surgeon and is not necessarily constructed for direct physical handling.

Figure 20:
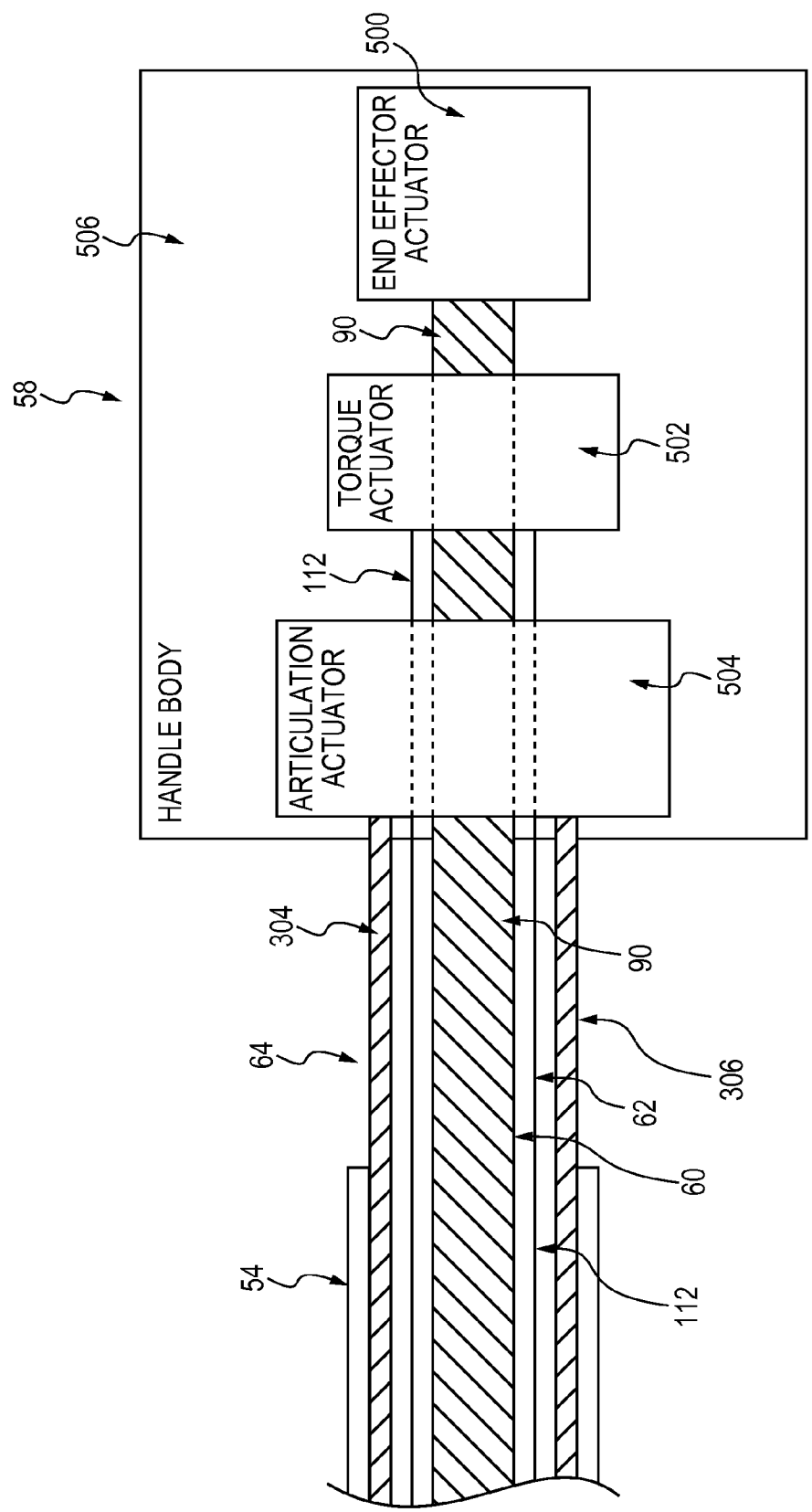
FIG. 20 is a schematic illustration of components of a handle assembly useful with the instrument of FIG. 1.

With this in mind, FIG. 20 schematically illustrates one embodiment of a handle assembly 58 in accordance with principles of the present disclosure, and includes an end effector actuator 500, a torque actuator 502, and an articulation actuator 504. The actuators 500-504 can be carried by a common handle body 506, and can be considered to be a component of the corresponding mechanism 60-64. For example, the end effector actuator 500 can be a switch or trigger that imparts a longitudinal pulling or pushing force (or other action such as delivery of energy) on to the rod 90. As described above, with embodiments in which the end effector 52 (FIG. 1) has a moveable-type construction, longitudinal movement of the rod 90 causes the end effector bodies 70, 72 (FIG. 1) to move relative to one another. The torque actuator 502 can also be a switch, trigger, wheel, bar, etc., the movement of which causes the torque shaft 112 to rotate. As described above, rotation of the torque shaft 112 causes the end effector 52 (FIG. 1) to rotate. Finally, the articulation actuator 504 can be a switch, trigger, wheel, bar, etc., the movement of which applies opposing tension forces on to the cable segments 304, 306. As described above, opposing tension forces in the cable segments 304, 306 cause the deflection section 66 (FIG. 1) to collectively articulate or bend, thus articulating the end effector 52 relative to the outer shaft 54. Additional actuators (not shown) can also be provided that promote user-prompted rotation of the outer shaft 54. With embodiments in which the surgical instrument 50 is intended to be directly and physically manipulated by the surgeon, the handle body 506 can be shaped and constructed to be held in the user's hand, for example as described in U.S. application Ser. No. 12/916,142 entitled "Articulating Laparoscopic Surgical Instruments," filed Oct. 29, 2010 and the teachings of which are incorporated herein by reference in its entirety. As one non-limiting example, the actuators 500-504 are generally labeled in FIG. 1. In other embodiments, the actuators 500-504 can be remotely controlled (e.g., electronically controlled, electro-mechanically controlled, pneumatically controlled, etc.) by the surgeon.

Usage Mode of Operation

Returning to FIGS. 3A-4B, during use, the surgical instruments 50 of the present disclosure can be employed to perform a variety of laparoscopic procedures, including single incision laparoscopic procedures. In a usage mode of the instrument 50, the torque mechanism 62 components are operatively connected with one another, and the articulation mechanism 64 components are operatively connected with one another, such as when the cable segments 302, 304 are placed under sufficient tension to draw the articulation members 310 into physical, operative contact with one another and the joint connectors 302, 304 (and thus the links 110 into physical, operative contact with one another and the drive bodies 114, 116).

In the usage mode, the end effector operation mechanism 60 can be actuated to operate the end effector 52 in the desired fashion. In this regard, the rod 90 moves independent of the torque and articulation mechanisms 62, 64, such that operation of the end effector 52 is in no way limited by the torque and articulation features of the instrument 50. Similarly, the torque mechanism 62 can be actuated to rotate the end effector 52 in a desired fashion, with the links 110, torque shaft 112, and drive bodies 114, 116 rotating independent of the end effector operation and articulation mechanisms 60, 64. Thus, rotation of the end effector 52 is in no way limited by the end effector operation and articulation features of the instrument 50. Finally, the articulation mechanism 64 can be actuated to articulate or bend the deflection section 66 in a desired fashion to spatially locate the end effector 52 relative to the outer shaft 54 as desired. Operation of the articulation mechanism 64 is independent of the end effector operation and torque mechanisms 60, 62, but causes a corresponding change in shape in one or more components of each mechanism 60, 62. For example, articulation or deflection of the deflection section 66 causes the individual links 110 to pivot relative to one another. Even with this pivoted movement, though, the links 110 remain operatively connected to one another (and to the drive bodies 114, 116) such that the torque mechanism 62 can be actuated to rotate the end effector 52 at any deflection shape. Similarly, rearrangement of the links 110 with articulation of the deflection section 66 is transferred as a force on to the rod 90. The rod 90 bends in response to this combination of forces, and remains available to transfer any push/pull force on to the end effector 52.

To facilitate traditional, single incision laparoscopic procedures, the instrument 50 has a low profile distal the handle assembly 58 (FIG. 1), in some embodiments. For example, the single incision procedure is oftentimes performed through a reduced-sized access port that effectively limits the maximum outer transverse dimension of any body inserted there through to be on the order of 5.5 mm consistent with this end-use limitation and as described above, the outer shaft 54 has an outer diameter of not more than 5.5 mm, and the end effector 52 and the wrist assembly 56 are configured so as to not exceed this 5.5 mm outer transverse dimension footprint. The end effector 52 can be manipulated to a closed state having a maximum transverse dimension of not greater than 5.5 mm. The clevis 230, the distal joint connector 302, the articulation members 310 and the proximal joint connector 300 effectively define a maximum transverse dimension of the wrist assembly 56 between the end effector 52 and the outer shaft 54, and do not present any transverse outer dimension greater than 5.5 mm. In other embodiments, one or more of the components has an outer transverse dimension greater than 5.5 mm.

Cleaning Mode of Operation

The optional flush port assembly 68 of FIG. 1 promotes cleaning and sterilization of portions of the instrument. For example, the flush port assembly 68 can include a flush port 520 attached to the outer shaft 54 proximate the handle assembly 58. The flush port 520 is fluidly open to a lumen of the shaft 54; cleaning liquid can thus be delivered through the flush port 520. In other embodiments, the flush port 520 can be assembled to other components of the instrument 50 otherwise fluidly open to the lumen of the outer shaft 54.

Figure 21:
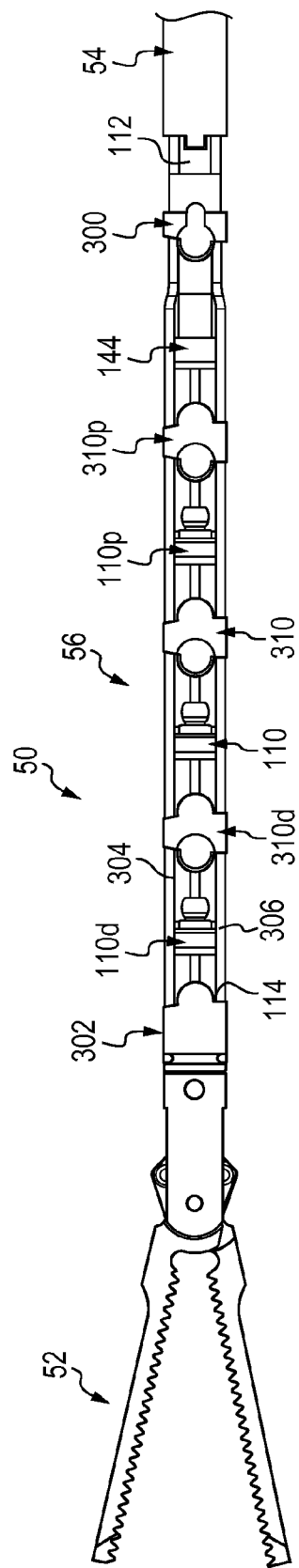
FIG. 21 is a side view of a portion of the instrument of FIG. 1 in an optional cleaning mode.

Cleaning and sterilization of the instrument 50 can be further enhanced by permitting selective separation of various components of the wrist assembly 56. For example, the handle assembly 58 can be configured to provide a user-selected cleaning mode in which the tension in one or both of the cable segments 304, 306 (FIG. 4A) is reduced or removed, generating slack in the cable segments 304, 306. This slack, in turn, allows adjacent ones of the articulating members 310 to be more completely separated from each other. The optional cleaning mode is reflected in FIG. 21. As shown, due to the slack in the cable segments 304, 306 the distal-most articulation member 310d can be physically spaced from the distal joint connector 302, the successive articulation members 310 can be physically spaced from one another, and the proximal-most articulation member 310p can be physically spaced from the proximal joint connector 300. Due to the seated couplings described above, this spacing also physically separates the distal-most link 110d from the distal drive body 114, the individual links 110 from one another, and the proximal-most link 110p from the proximal drive body 144. Further, the proximal joint connector 300 can be physically separated from the outer shaft 54 (e.g., with distal advancement of the torque shaft 112/proximal drive body 144 relative to the outer shaft 54). Surfaces of the now physically separated components are easily accessed for direct cleaning. Once cleaning is complete, the handle assembly 56 is returned to the usage mode reflected in the figures.

The articulating laparoscopic surgical instruments of the present disclosure provide marked improvements over previous designs. All operational features desired by surgeons for performing a single incision laparoscopic procedure are facilitated by a low profile wrist assembly connecting the end effector to the outer shaft. Further, instruments of the present disclosure are uniquely designed for reuse, including cleaning and sterilization.

Although the present disclosure has been described with reference to preferred embodiments, workers skilled in the art will recognize that changes can be made in form and detail without departing from the spirit and scope of the present disclosure. For example, while the wrist assembly has been described as connecting the articulation members over the torque links, in other constructions, a reverse relationship can be employed. Additionally, while the instruments have been described as including an end effector operation mechanism otherwise providing the elongated push/pull rod, in other embodiments, the rod can be replaced with different structure; with yet other constructions of instruments in accordance with principles of the present disclosure, the end effector operation mechanism is entirely omitted.

What is claimed is:

1. An articulating surgical instrument comprising:
    a handle;
    an elongated outer shaft extending from the handle to a shaft end;
    an end effector; and
    a wrist assembly connecting the end effector to the shaft end, the wrist assembly including:
    a torque mechanism including a plurality of links disposed between the shaft end and the end effector, the links collectively adapted to transfer a rotational force from a proximal-most link to the end effector,
    an articulation mechanism including a plurality of articulation members disposed between the shaft end and the end effector to collectively define a deflection section, the articulation mechanism adapted to spatially articulate the end effector relative to the shaft end;
    wherein the wrist assembly is configured such that the links articulate with articulation of the deflection section, and the links rotate independent of the articulation members;
    wherein each of the articulating members defines a central bore and opposing first and second side channels, where the central bore is sized to slidably receive a rod provided with an end effector operation mechanism of the wrist assembly, the articulation mechanism further including:
    a first cable segment threaded through the first side channel of each of the articulation members; and
    a second cable segment threaded through the second side channel of each of the articulation members;
    where the articulation mechanism is configured such that an increase of tension in the first cable segment and a decrease of tension in the second cable segment causes the deflection section to deflect in a direction of the first cable segment;
    where the wrist assembly is configured to provide:
    a usage mode in which adjacent ones of the links physically contact one another, and adjacent ones of the articulation members physically contact one another, wherein each of the links is associated with a corresponding one of the articulation members, and further wherein the articulation mechanism includes first and second cable segments slidably coupled to and interconnecting the articulation members, and still further wherein the usage mode include the cable segments being tensioned sufficiently such that the articulation members contact with one another and the links contact one another; and
    a cleaning mode in which sufficient slack in the cable segments provides that adjacent ones of the links are longitudinally spaced but not disassembled from one another and that adjacent ones of the articulation members are longitudinally spaced but not disassembled from one another.

2. The surgical instrument of claim 1, wherein a first one of the links is moveably associated with a corresponding first one of the articulation members such that the first link is forced to laterally translate by lateral translation of the first articulation member during operation of the articulation mechanism that causes the deflection section to articulate, and further wherein the first link rotates relative to the first articulation member during an operation of the torque mechanism that causes the end effector to rotate.

3. The surgical instrument of claim 2, wherein at least a portion of the first link is moveably disposed within the first articulation member.

4. The surgical instrument of claim 3, wherein the torque mechanism further includes a torque shaft disposed within the outer shaft and couplable to the proximal-most link.

5. The surgical instrument of claim 1, wherein the wrist assembly further includes:
    an end effector operation mechanism including a rod extending through the shaft and coupled to the end effector.

6. The surgical instrument of claim 5, wherein the links and the articulation members are disposed over the rod distal of the shaft end.

7. The surgical instrument of claim 6, wherein the outer shaft has an outer diameter of not more than 5.5 mm, and further wherein the rod is slidably disposed within the torque shaft.

8. The surgical instrument of claim 6, wherein the end effector includes a first body moveably associated with a second body and further wherein the end effector operation mechanism is configured such that longitudinal movement of the rod relative to the end effector causes the first body to move relative to the second body.

9. The surgical instrument of claim 1, wherein each of the links defines a male end portion opposite a female end portion, and further wherein when adjacent ones of the links are physically connected to one another, the male end portion of a first link is received within the female end of an immediately adjacent second link at a link interface such that the first link can laterally pivot relative the second link at the link interface, and a rotational force applied to the first link is transferred to the second link at the link interface.

10. The surgical instrument of claim 9, wherein the male end portion includes a polygonal ball head, and the female end portion forms a polygonal socket head configured to selectively receive the ball head.

11. The surgical instrument of claim 10, wherein each link defines a longitudinal axis, and further wherein the polygonal ball head has a polygonal shaped cross-section in a plane perpendicular to the longitudinal axis.

12. The surgical instrument of claim 11, wherein a cross-section of the ball head in a plane passing through the longitudinal axis has curved lateral edges.

13. The surgical instrument of claim 12, wherein the socket head defines a receptacle having the polygonal shape such that when the male end portion of the first link is received within the female end portion of the second link, rotation of the of the first link is directly transferred to the second link via a locked interface between the polygonal shapes, and the first link can pivot relative to the second link via the curved lateral edges sliding relative to the receptacle.

14. The surgical instrument of claim 9, wherein the torque mechanism further includes a connector fixed to and extending proximally from the end effector, the connector forming one of the male end portion and the female end portion.

15. The surgical instrument of claim 1, wherein each of the plurality of links is discrete from a remainder of the plurality of links.

16. The surgical instrument of claim 1, wherein the cable segments are defined by a single cable.

17. The surgical instrument of claim 1, wherein the wrist assembly is configured such that during operation of the articulation mechanism to change a shape of the deflection section, the deflection section applies a force on to the plurality of links, with the plurality of links collectively assuming a shape of the deflection section.

18. The surgical instrument of claim 17, wherein the wrist assembly further includes:
an end effector operation mechanism including a rod extending through the shaft and coupled to the end effector such that longitudinal movement of the rod relative to the end effector causes the first body to move relative to the second body;
wherein during operation of the articulation mechanism to change a shape of the deflection section, a portion of the rod surrounded by the deflection section assumes a shape of the deflection section.

19. The surgical instrument of claim 1, wherein each of the mechanisms further includes an actuator carried by the handle and configured to facilitated user-controlled operation of the corresponding mechanism.

20. The surgical instrument of claim 1, wherein the links are configured such that upon transitioning from the cleaning mode to the usage mode in response to increased tension of the cable segments, adjacent links self-align and engage with one another.

* * * * *